United States Patent
Willard et al.

(10) Patent No.: US 10,945,786 B2
(45) Date of Patent: Mar. 16, 2021

(54) BALLOON CATHETERS WITH FLEXIBLE CONDUCTING WIRES AND RELATED METHODS OF USE AND MANUFACTURE

(71) Applicant: Boston Scientific Scimed, Inc., Maple Grove, MN (US)

(72) Inventors: Martin R. Willard, Burnsville, MN (US); Derek C. Sutermeister, Ham Lake, MN (US); Kenneth R. Larson, Grand Rapids, MN (US); Timothy A. Ostroot, Cokato, MN (US); Patrick A. Haverkost, Brooklyn Center, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1751 days.

(21) Appl. No.: 14/516,014

(22) Filed: Oct. 16, 2014

(65) Prior Publication Data

US 2015/0112328 A1    Apr. 23, 2015

Related U.S. Application Data

(60) Provisional application No. 61/893,032, filed on Oct. 18, 2013.

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00434* (2013.01);
(Continued)

(58) Field of Classification Search
CPC .. A61B 2018/00214; A61B 2018/0022; A61B 2018/00077; A61B 2018/00434;
(Continued)

(56) References Cited

U.S. PATENT DOCUMENTS 164,184 A    6/1875   Kiddee
852,787 A    5/1907   Hoerner
(Continued)

FOREIGN PATENT DOCUMENTS

DE    10038737 A1    2/2002
EP    1053720 A1    11/2000
(Continued)

OTHER PUBLICATIONS

US 8,398,630 B2, 03/2013, Demarais et al. (withdrawn)
(Continued)

*Primary Examiner* — Jaymi E Della

(74) *Attorney, Agent, or Firm* — Kacvinsky Daisak Bluni PLLC

(57) ABSTRACT

A medical device and related methods of use or manufacture are disclosed. The medical device may include an intravascular catheter for nerve modulation. The medical device includes an elongate shaft having a proximal end region, a distal end region, and a lumen extending therebetween. An expandable member is coupled to the distal end region of the elongate shaft. One or more electrical conductors extend from the proximal end region of the elongate shaft to the expandable member. The one or more electrical conductors may have a distal end region secured directly to an outer surface the expandable member. One or more energy delivery regions are positioned on the expandable member and coupled to the one or more electrical conductors.

17 Claims, 7 Drawing Sheets

(52) U.S. Cl.
CPC .......... *A61B 2018/00577* (2013.01); *A61B 2018/00815* (2013.01)

(58) Field of Classification Search
CPC ...... A61B 2018/00815; A61B 18/1492; A61B 2018/00577
See application file for complete search history.

(56) References Cited

U.S. PATENT DOCUMENTS

| | | |
|---|---|---|
| 921,973 A | 5/1909 | Gillett et al. |
| 976,733 A | 11/1910 | Gilliland |
| 1,167,014 A | 1/1916 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,290,427 A | 9/1981 | Chin |
| 4,402,686 A | 9/1983 | Medel |
| 4,483,341 A | 11/1984 | Witteles et al. |
| 4,531,943 A | 7/1985 | Van Tassel et al. |
| 4,574,804 A | 3/1986 | Kurwa |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,765,331 A | 8/1988 | Petruzzi et al. |
| 4,770,653 A | 9/1988 | Shturman |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,890,623 A | 1/1990 | Cook et al. |
| 4,920,979 A | 5/1990 | Bullara et al. |
| 4,938,766 A | 7/1990 | Jarvik |
| 4,955,377 A | 9/1990 | Lennox et al. |
| 4,976,711 A | 12/1990 | Parins et al. |
| 5,034,010 A | 7/1991 | Kittrell et al. |
| 5,052,402 A | 10/1991 | Bencini et al. |
| 5,053,033 A | 10/1991 | Clarke et al. |
| 5,071,424 A | 12/1991 | Reger et al. |
| 5,074,871 A | 12/1991 | Groshong et al. |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,139,496 A | 8/1992 | Hed |
| 5,143,836 A | 9/1992 | Hartman et al. |
| 5,156,610 A | 10/1992 | Reger et al. |
| 5,158,564 A | 10/1992 | Schnepp-Pesch |
| 5,170,802 A | 12/1992 | Mehra |
| 5,178,620 A | 1/1993 | Eggers et al. |
| 5,178,625 A | 1/1993 | Groshong et al. |
| 5,190,540 A | 3/1993 | Lee |
| 5,211,651 A | 5/1993 | Reger et al. |
| 5,234,407 A | 8/1993 | Teirstein et al. |
| 5,238,004 A | 8/1993 | Sahatjian et al. |
| 5,242,441 A | 9/1993 | Avitall |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,277,201 A | 1/1994 | Stern et al. |
| 5,282,484 A | 2/1994 | Reger et al. |
| 5,286,254 A | 2/1994 | Shapland et al. |
| 5,290,306 A | 3/1994 | Trotta et al. |
| 5,295,484 A | 3/1994 | Marcus |
| 5,297,564 A | 3/1994 | Love et al. |
| 5,300,068 A | 4/1994 | Rosar et al. |
| 5,301,683 A | 4/1994 | Durkan |
| 5,304,115 A | 4/1994 | Pflueger et al. |
| 5,304,120 A * | 4/1994 | Crandell ............ A61M 29/02 604/104 |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,324,255 A | 6/1994 | Passafaro et al. |
| 5,326,341 A | 7/1994 | Lew et al. |
| 5,326,342 A | 7/1994 | Plueger et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,380,274 A | 1/1995 | Nita et al. |
| 5,380,319 A | 1/1995 | Saito et al. |
| 5,382,228 A | 1/1995 | Nita et al. |
| 5,383,874 A | 1/1995 | Jackson et al. |
| 5,383,917 A | 1/1995 | Desai et al. |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,417,672 A | 5/1995 | Nita et al. |
| 5,419,767 A | 5/1995 | Eggers et al. |
| 5,427,118 A | 6/1995 | Nita et al. |
| 5,432,876 A | 7/1995 | Appeldorn et al. |
| 5,441,498 A | 8/1995 | Perkins et al. |
| 5,447,509 A | 9/1995 | Mills et al. |
| 5,451,207 A | 9/1995 | Yock et al. |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,682 A | 10/1995 | Edwards et al. |
| 5,457,042 A | 10/1995 | Hartman et al. |
| 5,471,982 A | 12/1995 | Edwards et al. |
| 5,474,530 A | 12/1995 | Passafaro et al. |
| 5,478,351 A | 12/1995 | Meade et al. |
| 5,496,311 A | 3/1996 | Abele et al. |
| 5,496,312 A | 3/1996 | Klicek et al. |
| 5,498,261 A | 3/1996 | Strul |
| 5,505,201 A | 4/1996 | Grill et al. |
| 5,505,730 A | 4/1996 | Edwards |
| 5,507,744 A | 4/1996 | Tay et al. |
| 5,512,051 A | 4/1996 | Wang et al. |
| 5,522,873 A | 6/1996 | Jackman et al. |
| 5,531,520 A | 7/1996 | Grimson et al. |
| 5,540,656 A | 7/1996 | Pflueger et al. |
| 5,540,679 A | 7/1996 | Fram et al. |
| 5,540,681 A | 7/1996 | Strul et al. |
| 5,542,917 A | 8/1996 | Nita et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |

(56) References Cited

U.S. PATENT DOCUMENTS

| | | |
|---|---|---|
| 5,609,606 A | 3/1997 | O'Boyle et al. |
| 5,613,979 A | 3/1997 | Trotta et al. |
| 5,626,576 A | 5/1997 | Janssen |
| 5,630,837 A | 5/1997 | Crowley |
| 5,637,090 A | 6/1997 | McGee et al. |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,672,174 A | 9/1997 | Gough et al. |
| 5,676,693 A | 10/1997 | Lafontaine |
| 5,678,296 A | 10/1997 | Fleischhacker |
| 5,681,282 A | 10/1997 | Eggers et al. |
| RE35,656 E | 11/1997 | Feinberg |
| 5,687,737 A | 11/1997 | Branham et al. |
| 5,688,266 A | 11/1997 | Edwards et al. |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,706,809 A | 1/1998 | Littmann et al. |
| 5,713,942 A * | 2/1998 | Stern ............... A61B 18/1442 607/98 |
| 5,715,819 A | 2/1998 | Svenson et al. |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,903 A | 4/1998 | Stern et al. |
| 5,748,347 A | 5/1998 | Erickson |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,880 A | 6/1998 | Truckai et al. |
| 5,775,338 A | 7/1998 | Hastings |
| 5,776,174 A | 7/1998 | Van Tassel |
| 5,779,698 A * | 7/1998 | Clayman ............... A61B 17/22 604/114 |
| 5,782,760 A | 7/1998 | Schaer |
| 5,785,702 A | 7/1998 | Murphy et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,306 A | 9/1998 | Shapland et al. |
| 5,810,802 A | 9/1998 | Panescu et al. |
| 5,810,803 A | 9/1998 | Moss et al. |
| 5,810,810 A | 9/1998 | Tay et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,397 A | 3/1999 | Edelman et al. |
| 5,879,348 A | 3/1999 | Owens et al. |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford, III et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,924,424 A | 7/1999 | Stevens et al. |
| 5,925,038 A | 7/1999 | Panescu et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,941 A | 9/1999 | Ream et al. |
| 5,957,969 A | 9/1999 | Warner et al. |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littrnann et al. |
| 5,967,984 A | 10/1999 | Chu et al. |
| 5,971,975 A | 10/1999 | Mills et al. |
| 5,972,026 A | 10/1999 | Laufer et al. |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy et al. |
| 6,004,269 A | 12/1999 | Crowley et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,014,590 A | 1/2000 | Whayne et al. |
| 6,022,309 A | 2/2000 | Celliers et al. |
| 6,024,740 A | 2/2000 | Lesh et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,041,260 A | 3/2000 | Stern et al. |
| 6,050,994 A | 4/2000 | Sherman et al. |
| 6,056,744 A | 5/2000 | Edwards |

(56) References Cited

U.S. PATENT DOCUMENTS

| | | |
|---|---|---|
| 6,056,746 A | 5/2000 | Goble et al. |
| 6,063,085 A | 5/2000 | Tay et al. |
| 6,066,096 A | 5/2000 | Smith et al. |
| 6,066,139 A | 5/2000 | Ryan et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,091,995 A | 7/2000 | Ingle et al. |
| 6,093,166 A | 7/2000 | Knudson et al. |
| 6,096,021 A | 8/2000 | Helm et al. |
| 6,099,526 A | 8/2000 | Whayne et al. |
| 6,102,908 A | 8/2000 | Tu et al. |
| 6,106,477 A | 8/2000 | Miesel et al. |
| 6,110,187 A | 8/2000 | Donlon et al. |
| 6,110,192 A | 8/2000 | Ravenscroft et al. |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,725 A | 10/2000 | Tu et al. |
| 6,135,997 A | 10/2000 | Laufer et al. |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,505 B2 | 9/2002 | McGovern et al. |

(56) References Cited

U.S. PATENT DOCUMENTS

| | | |
|---|---|---|
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |
| 6,484,052 B1 | 11/2002 | Visuri et al. |
| 6,485,489 B2 | 11/2002 | Teirstein et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,803 B1 | 1/2003 | Horikawa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,527,765 B2 | 3/2003 | Kelman et al. |
| 6,527,769 B2 | 3/2003 | Langberg et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,577,902 B1 | 6/2003 | Laufer et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,238 B2 | 7/2003 | Edwards et al. |
| 6,592,526 B1 | 7/2003 | Lenker |
| 6,592,567 B1 | 7/2003 | Levin et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,056 B2 | 8/2003 | Eidenschink et al. |
| 6,605,084 B2 | 8/2003 | Acker et al. |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,634,363 B1 | 10/2003 | Danek et al. |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,695,857 B2 | 2/2004 | Gifford, III et al. |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,736,811 B2 | 5/2004 | Panescu et al. |
| 6,743,184 B2 | 6/2004 | Sampson et al. |
| 6,746,401 B2 | 6/2004 | Panescu |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Doscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |

(56) References Cited

U.S. PATENT DOCUMENTS

| | | |
|---|---|---|
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,889,694 B2 | 5/2005 | Hooven |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | Lafontaine et al. |
| 6,923,808 B2 | 8/2005 | Taimisto |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,949,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,378 B2 | 2/2006 | Yon et al. |
| 7,006,858 B2 | 2/2006 | Silver et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |

(56) References Cited

U.S. PATENT DOCUMENTS

| | | |
|---|---|---|
| 7,282,213 B2 | 10/2007 | Schroeder et al. |
| 7,285,119 B2 | 10/2007 | Stewart et al. |
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,480 B2 | 1/2008 | Eidenschink et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| RE40,863 E | 7/2009 | Tay et al. |
| 7,556,624 B2 | 7/2009 | Laufer et al. |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,686,841 B2 | 3/2010 | Eidenschink et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |

(56) References Cited

U.S. PATENT DOCUMENTS

| | | |
|---|---|---|
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,043,673 B2 | 10/2011 | Lee et al. |
| 8,048,144 B2 | 11/2011 | Thistle et al. |
| 8,052,636 B2 | 11/2011 | Moll et al. |
| 8,052,700 B2 | 11/2011 | Dunn |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,168,275 B2 | 5/2012 | Lee et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |

(56) References Cited

U.S. PATENT DOCUMENTS

| | | |
|---|---|---|
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0050635 A1 | 3/2003 | Truckai et al. |
| 2003/0065317 A1 | 4/2003 | Rudie et al. |
| 2003/0092995 A1 | 5/2003 | Thompson |
| 2003/0139689 A1 | 7/2003 | Shturman et al. |
| 2003/0195501 A1 | 10/2003 | Sherman et al. |
| 2003/0199747 A1 | 10/2003 | Michlitsch et al. |
| 2003/0229340 A1 | 12/2003 | Sherry et al. |
| 2003/0233099 A1 | 12/2003 | Danaek et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0243022 A1 | 12/2004 | Carney et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0080374 A1 | 4/2005 | Esch et al. |
| 2005/0096647 A1 | 5/2005 | Steinke et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2005/0273149 A1 | 12/2005 | Tran et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0083194 A1 | 4/2006 | Dhrimaj et al. |
| 2006/0085054 A1 | 4/2006 | Zikorus et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0182873 A1 | 8/2006 | Klisch et al. |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0067883 A1 | 3/2007 | Sretavan |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225781 A1 | 9/2007 | Saadat et al. |

(56) References Cited

U.S. PATENT DOCUMENTS

| | | |
|---|---|---|
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0077095 A1 | 3/2008 | Kirchhofer |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khun-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1* | 6/2010 | Jarrard ............... A61B 18/1492 606/33 |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0204560 A1* | 8/2010 | Salahieh ................. A61B 5/01 600/373 |
| 2010/0217162 A1 | 8/2010 | Hissong et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |

(56) References Cited

U.S. PATENT DOCUMENTS

| | | |
|---|---|---|
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0065506 A1 | 3/2012 | Smith |
| 2012/0065554 A1 | 3/2012 | Pikus |
| 2012/0071870 A1* | 3/2012 | Salahieh ............ A61B 1/00181 606/33 |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2012/0310233 A1* | 12/2012 | Dimmer ............ A61B 18/1492 606/33 |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0085493 A1 | 4/2013 | Bloom et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |
| 2014/0074083 A1 | 3/2014 | Horn et al. |

FOREIGN PATENT DOCUMENTS

| | | |
|---|---|---|
| EP | 1180004 A1 | 2/2002 |
| EP | 1335677 B1 | 8/2003 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |

(56) References Cited

FOREIGN PATENT DOCUMENTS

| | | | |
|---|---|---|---|
| EP | 2037840 B1 | 12/2011 | |
| EP | 2204134 B1 | 4/2012 | |
| EP | 2320821 B1 | 10/2012 | |
| GB | 2456301 A | 7/2009 | |
| WO | 1994023794 A1 | 10/1994 | |
| WO | 1995031142 A1 | 11/1995 | |
| WO | 9858588 A1 | 12/1998 | |
| WO | 9900060 A1 | 1/1999 | |
| WO | 9935986 | 7/1999 | |
| WO | 0047118 A1 | 8/2000 | |
| WO | 0066021 | 11/2000 | |
| WO | 0195820 | 12/2001 | |
| WO | 03026525 A1 | 4/2003 | |
| WO | 2004100813 A2 | 11/2004 | |
| WO | 2004110258 A2 | 12/2004 | |
| WO | 2005041810 | 5/2005 | |
| WO | 2006105121 A2 | 10/2006 | |
| WO | 2008014465 A2 | 1/2008 | |
| WO | 2009121017 A1 | 10/2009 | |
| WO | 2010067360 A2 | 6/2010 | |
| WO | 2010102310 A2 | 9/2010 | |
| WO | 2010132703 | 11/2010 | |
| WO | 2011005901 A2 | 1/2011 | |
| WO | 2011053757 A1 | 5/2011 | |
| WO | 2011053772 A1 | 5/2011 | |
| WO | 2011060200 A1 | 5/2011 | |
| WO | 2011091069 A1 | 7/2011 | |
| WO | 2011130534 A2 | 10/2011 | |
| WO | 2012019156 A1 | 2/2012 | |
| WO | 2013049601 A2 | 4/2013 | |
| WO | 2013134780 A1 | 9/2013 | |

OTHER PUBLICATIONS

CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50(2): 218-223, Feb. 2003.
Lazebnik et al., "Tissue Strain Analytics Virtual Touch Tissue Imaging and Qualification," Siemens Whitepaper, 7 pages, Oct. 2008.
Han et al., "Third-Generation Cryosurgery for Primary and Recurrent Prostate Caner," BJU International, vol. 93: 14-18, Sep. 23, 2003.
Zhou et al., "Mechanism Research of Cryoanalgesia," Neurological Research, Forefront Publishing Group, 17: 307-311, Aug. 1995.
Florete, "Cryoblative Procedure for Back Pain," Jacksonville Medicine, Oct. 1998, 10 pages, printed Dec. 2009.
Stevenson, "Irrigated RF Ablation: Power Titration and Fluid Management for Optimal Safety Efficacy," 4 pages, 2005.
Giliatt et al., "The Cause of Nerve Damage in Acute Compression," Trans Am Neural Assoc, 99: 71-4, 1974.
Omura et al., "A Mild Acute Compression Induces Neurapraxia in Rat Sciatic Nerve," The International Journal of Neuroscience, vol. 114 (12):1561-1572, Dec. 2004.
Baun, "Interaction with Soft Tissue," Principles of General & Vascular Sonography, Chapter 2, pp. 23-24, Before Mar. 2012.
Blue Cross Blue Shield Medical Policy, "Surgery Section—MRI-Guided Focused Ultrasound (MRgFUS) for the Treatment of Uterine Fibroids and Other Tumors," 5 pages, printed Oct. 19, 2009.
Gentry et al., "Combines 3D Intracardiac Echo and Ultrasound Ablation," Medical Imaging 2003: Ultrasonic and Signal Processing, 5035: 166-173, 2003.
Lafon et al., "Optmizing the Shape of Ultrasound Transducers for Interstitial Thermal Ablations," MEd Phys. Mar. 2002; 29(3): 290-7 (abstract only), Mar. 2002.
G. Ter Haar, "Ultrasound Focal Beam Surgery," Ultrasound in Med. & Biol., 1995, 21(9): 1089-1100.

Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, 7562: 1-10, 2010.
Zhou et al., "Non-Thermal Ablation of Rabbit Liver VX2 Tumore by Pulsed High Intensity Focused Ultrasound Contrast Agent: Pathological Characteristics," World Journal of Gastroenterology, 14(43): 6743-6747, Nov. 21, 2008.
Van Den Berg, "Light echoes image the human body," OLE, p. 35-37, Oct. 2001.
"IntraLuminal: Products," IntraLuminal Therapeutics, Inc., p. 1-9, 2003.
"Laser Catheter to Aid Coronary Surgery," TechTalk: MIT, p. 1-4, Jan. 9, 1991.
"Optical Coherence Tomography: LightLab Imaging Starts US Cardiology Clinical Investigations," LightLab Imaging Technology Company Press Release, Jun. 25, 2002, <http://www.lightlabimaging.com/press/cardtrails.html> 2 pages.
"Optical Coherence Tomography: LightLab Sees Bright Prospects for Cardiac Application of OCT Technology," LightLab Imaging Technology, The Gray Sheet, Medical Devices, Diagnostics, & Instrumentation, 27(35), Aug. 27, 2001, <http://www.lightlabimaging.com/press/graysheet.html> 1 page.
"Products—Functional Measurement," VOLCANO Functional Measurement Products US, p. 1-2, Mar. 24, 2003.
Brown et al., "Radiofrequency capacitive heaters: the effect of coupling medium resistivity on power absorption along a mouse leg," Physics in Medicine and Biology, 38: 1-12, 1993.
Carrington, "Future of CVI: It's all about plaque: Identification of vulnerable lesions, not 'rusty pipes,' could become cornerstone of preventive cardiology," Diagnostic Imaging Special Edition Forum, 5 pages total, retrieved on Sep. 3, 2003.
Chen et al., "Percutaneous pulmonary artery denervation completely abolishes experimental pulmonary arterial hypertension in vivo," EuroIntervention, p. 1-8, 2013.
Cimino, "Preventing plaque attack," Mass High Tech, 3 pages total, retrieved on Sep. 3, 2003 <http://Masshightech.com/displayarticledetail.ap?art_id=52283&cat_id=10>, 2001.
Dahm et al., "Relation of Degree of Laser Debulking of In-Stent Restenosis as a Predictor of Restenosis Rate," The American Journal of Cardiology, 90:68-70, 2002.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," 7 pages, Fourth Edition, Oct. 1986.
Pieper et al. "Design and implementation of a new computerized system for intraoperative cardiac mapping", J. Appl. Physiol. 71(4): 1529-1539, 1991.
Fournier-Desseux et al., "Assessment of 1-lead and 2-lead electrode patterns in electrical impedance endotomography," Physiological Measurement, Institute of Physics Publishing, 26:337-349, 2005.
Fram et al., "Feasibility of Radiofrequency Powered, Thermal Balloon Ablation of Atrioventricular Bypass Tracts Via the Coronary Sinus: In Vivo Canine Studies," PACE, 18:1518-1530, Aug. 1995.
Fram et al., "Low Pressure Radiofrequency Balloon Angioplasty: Evaluation in Porcine Peripheral Arteries," JACC, American College of Cardiology, 21(6):1512-1521, 1993.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," p. 1-21, 1999.
Gabriel, "Appendix C: Modeling the frequency dependence of the dielectric properties to a 4 dispersions spectrum," p. 1-49, Nov. 6, 1997.

(56) References Cited

OTHER PUBLICATIONS

Gregory et al., "Liquid Core Light Guide for Laser Angioplasty," The Journal of Quantum Electronics, 26 (12):2289-2296, Dec. 1990.
Kaplan et al., "Healing after Arterial Dilatation with Radiofrequency Thermal and Nonthermal Balloon Angioplasty Syterns," Journal of Investigative Surgery, 6:33-52, 1993.
Kolata, "New Studies Question Value of Opening Arteries," The New York Times [online], 5 pages total, <http://nytimes.corn/2004/03/21/health/21HEAR.html?ei=5070&en=641bc03214e&ex=11067>, Mar. 21, 2004.
Konings et al., "Development of an Intravascular Impedance Catheter for Detection of Fatty Lesions in Arteries," IEEE Transactions on Medical Imaging, 16(4):439-444, Aug. 1997.
Kurtz et al., "Lamellar Refractive Surgery with Scanned Intrastromal Picosecond and Femtosecond Laser Pulses in Animal Eyes," Journal of Refractive Surgery, 14:541-548, Sep./Oct. 1998.
Lee et al., "Thermal Compression and Molding of Atherosclerotic Vascular Tissue With Use of Radiofrequency Energy: Implications for Radiofrequency Balloon Angioplasty," JACC, American College of Cardiology, 13(5):1167-1175, 1989.
Lima et al., "Efficacy and Safety of Oral Sirolimus to Treat and Prevent In-Stent Restenosis: A Pilot Study Results," American Heart Association, p. 2929, 2002.
Lima et al., "Systemic Immunosuppression Inhibits In-Stent Coronary Intimal Proliferation in Renal Transplant Patients," American Heart Association, p. 2928, 2002.
Morice et al., "A Randomized Comparison of a Sirolimus-Eluting Stent With a Standard Stent for Coronary Revascularization," The New England Journal of Medicine, 346(23):1773-1780, Jun. 6, 2002.
Muller-Leisse et al., "Effectiveness and Safety of Ultrasonic Atherosclerotic Plaque Ablation: In Vitro Investigation," CardioVascular and Interventional Radiology, 16:303-307, 1993.
Nair et al., "Regularized Autoregressive Analysis of Intravascular Ultrasound Backscatter: Improvement in Spatial Accuracy of Tissue Maps," IEEE Transactions on Ultrasonics, 51(4):420-431, Apr. 2004.
Popma et al., "Percutaneous Coronary and Valvular Intervention," Braunwald's Heart Disease: A Textbook of Cardiovascular Medicine, 7th edition, p. 1364-1405, 2005.

Resar et al., "Endoluminal Sealing of Vascular Wall Disruptions With Radiofrequency-Heated Balloon Angioplasty," Catheterization and Cardiovascular Diagnosis, 29:161-167, 1993.
Romer et al., "Histopathology of Human Coronary Atherosclerosis by Quantifying Its Chemical Composition With Raman Spectroscopy," Circulation, 97:878-885, 1998.
Schauerte et al., "Catheter Ablation of Cardiac Autonomic Nerves for Prevention of Vagal Atrial Fibrillation," Circulation, 102:2774-2780, 2000.
Scheller et al., "Intracoronary Paclitaxel Added to Contrast Media Inhibits In-Stent Restenosis of Porcine Coronary Arteries," American Heart Association, p. 2227, 2002.
Scheller et al., "Potential solutions to the current problem: coated balloon," Eurolntervention, 4(Supplement C): C63-C66, 2008.
Shaffer, "Scientific basis of laser energy," Clinics in Sports Medicine, 21:585-598, 2002.
Shmatukha et al., "MRI temperature mapping during thermal balloon angioplasty," Physics in Medicine and Biology, 51:N163-N171, 2006.
Slager et al., "Vaporization of Atherosclerotic Plaques by Spark Erosion," J Am Coll Cardiol, p. 21-25, 1985.
Stiles et al., "Simulated Characterization of Atherosclerotic Lesions in the Coronary Arteries by Measurement of Bioimpedance," IEEE Transactions on Biomedical Engineering, 50(7): 916-921, Jul. 2003.
Suselbeck et al., "In vivo intravascular electric impedance spectroscopy using a new catheter with integrated microelectrodes," Basic Res Cardiol, 100:28-34, 2005.
Suselbeck et al., "Intravascular electric impedance spectroscopy of atherosclerotic lesions using a new impedance catheter system," Basic Res Cardiol, 100:446-452, 2005.
Tepe et al., "Local Delivery of Paclitaxel to Inhibit Restenosis during Angioplasty of the Leg," The New England Journal of Medicine, 358:689-699, 2008.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.

* cited by examiner

BALLOON CATHETERS WITH FLEXIBLE CONDUCTING WIRES AND RELATED METHODS OF USE AND MANUFACTURE

CROSS-REFERENCE TO RELATED APPLICATIONS

This application claims priority under 35 U.S.C. § 119 to U.S. Provisional Application Ser. No. 61/893,032, filed Oct. 18, 2013, the entirety of which is incorporated herein by reference.

TECHNICAL FIELD

The invention generally pertains to percutaneous and intravascular devices for nerve modulation and/or ablation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a medical device for sympathetic nerve modulation and/or ablation. The medical device may include an intravascular catheter for nerve modulation. The medical device includes an elongate shaft having a proximal end region, a distal end region, and a lumen extending therebetween. An expandable member is coupled to the distal end region of the elongate shaft. One or more electrical conductors extend from the proximal end region of the elongate shaft to the expandable member, the one or more electrical conductors having a distal end region secured to an outer surface of the expandable member. One or more energy delivery regions are positioned on the expandable member and are coupled to the one or more electrical conductors.

Another example medical device may include a medical device for modulating nerves. The medical device includes an elongate shaft having a proximal end region, a distal end region, and a lumen extending therebetween. An inflatable balloon is coupled to the distal end region of the elongate shaft. One or more wire conductors have a proximal end and a distal end and are covered with an insulating material. The one or more wire conductors extend from the proximal end region of the elongate shaft to the expandable member. At least a portion of the one or more wire conductors is free from the insulating material defining one or more energy delivery regions adjacent the distal end of the one or more wire conductors.

Still another example medical device may include a medical device for modulating nerves. The medical device includes an elongate shaft having a proximal end region, a distal end region, and a lumen extending therebetween. An inflatable balloon is coupled to the distal end region of the elongate shaft. One or more round wire conductors have a proximal end and a distal end and are covered with an insulating material. The one or more round wire conductors extend from the proximal end region of the elongate shaft to the expandable member. At least a portion of the one or more round wire conductors is wound in a serpentine manner and free from the insulating material defining one or more energy delivery regions adjacent the distal end of the one or more wire conductors. One or more temperature sensors are positioned adjacent to at least one of the one or more energy delivery regions. The one or more energy delivery regions are arranged in bipolar pairs.

The above summary of some example embodiments is not intended to describe each disclosed embodiment or every implementation of the disclosed subject matter. The Figures, and Detailed Description, which follow, more particularly exemplify these embodiments

BRIEF DESCRIPTION OF THE DRAWINGS

The disclosed subject matter may be more completely understood in consideration of the following detailed description of various embodiments in connection with the accompanying drawings, in which.

Figure 1:
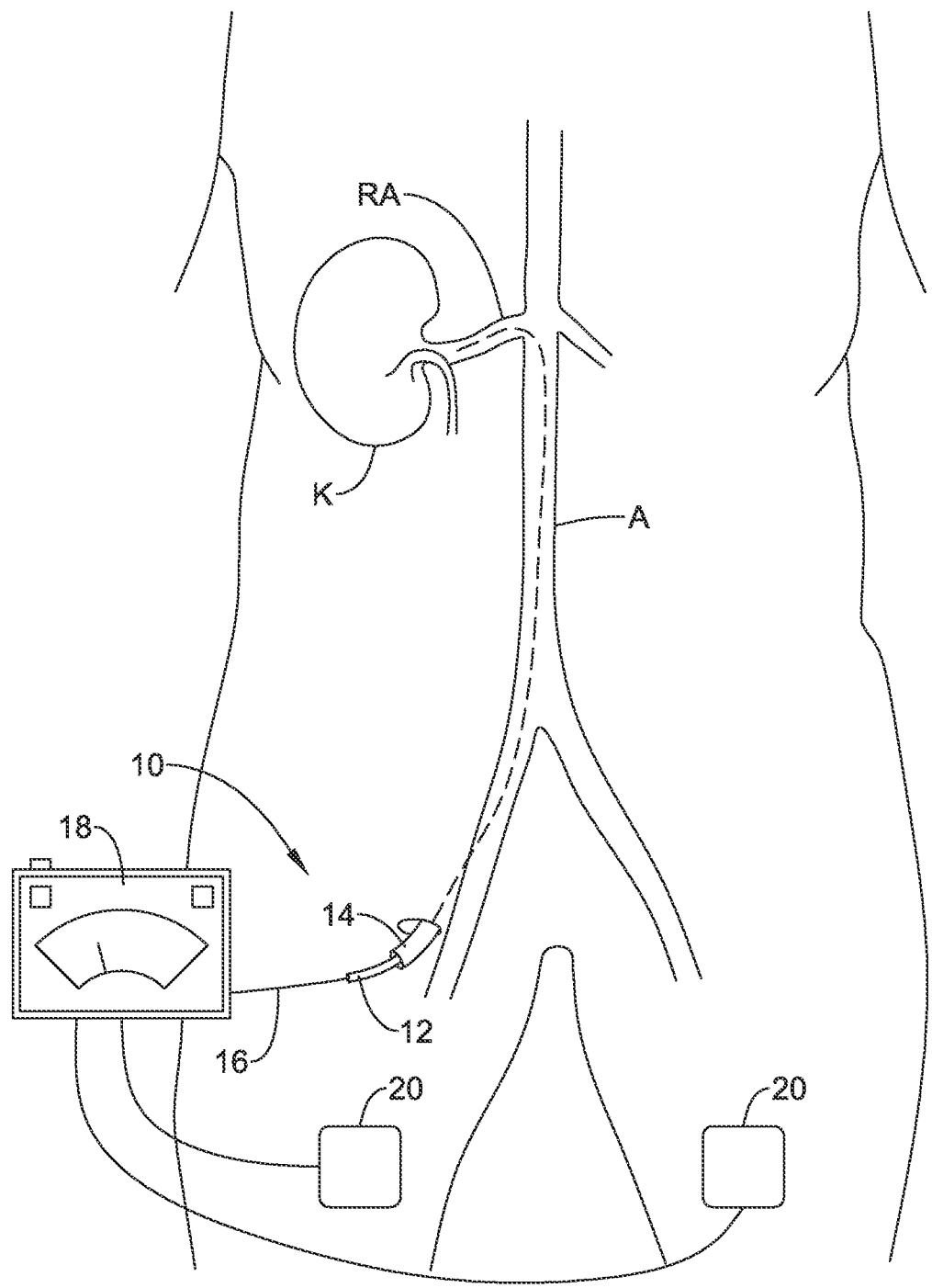
FIG. 1 is a schematic view illustrating a sympathetic nerve modulation system in situ.

While the disclosed subject matter is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, wherein like reference numerals indicate like elements throughout the several views. The drawings, which are not necessarily to scale, are not intended to limit the scope of the claimed invention. The detailed description and drawings illustrate exemplary embodiments of the claimed invention. Those skilled in the art will recognize that the various elements described and/or shown may be arranged in various combinations and configurations without departing from the scope of the disclosure. The detailed description and drawings illustrate example embodiments of the claimed invention.

All numbers or values are herein assumed to be modified by the term "about." The disclosure of numerical ranges by endpoints includes all numbers subsumed within that range (e.g., 1 to 5 includes 1, 1.5, 2, 2.75, 3, 3.80, 4, and 5).

As used in this specification and the appended claims, the singular indefinite articles "a", "an", and the definite article "the" should be considered to include or otherwise cover both single and plural referents unless the content clearly dictates otherwise. In other words, these articles are applicable to one or more referents. As used in this specification and the appended claims, the term "or" is generally employed to include or otherwise cover "and/or" unless the content clearly dictates otherwise.

References in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases do not necessarily refer to the same embodiment. Further, any particular feature, structure, or characteristic described in connection with a particular embodiment is intended to be applied, incorporated or substituted into other embodiments, whether or not explicitly described, unless clearly stated to the contrary.

Certain treatments are aimed at the temporary or permanent interruption or modification of select nerve function. In some instances, the nerves are sympathetic nerves. One example treatment is renal nerve ablation, which is sometimes used to treat conditions related to hypertension, congestive heart failure, diabetes, or other conditions impacted by high blood pressure or salt retention. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Some embodiments of the present disclosure relate to a power generating and control apparatus, often for the treatment of targeted tissue in order to achieve a therapeutic effect. In some embodiments, the target tissue is tissue containing or proximate to nerves. In one embodiment, the target tissue includes renal arteries and associated renal nerves. In other embodiments, the target tissue is sympathetic nerves including, for example, sympathetic nerves disposed adjacent to blood vessels. In still other embodiments the target tissue is luminal tissue, which may further comprise diseased tissue such as that found in arterial disease.

In some embodiments of the present disclosure, the ability to deliver energy in a targeted dosage may be used for nerve tissue in order to achieve beneficial biologic responses. For example, chronic pain, urologic dysfunction, hypertension, and a wide variety of other persistent conditions are known to be affected through the operation of nervous tissue. For example, it is known that chronic hypertension that may not be responsive to medication may be improved or eliminated by disabling excessive nerve activity proximate to the renal arteries. It is also known that nervous tissue does not naturally possess regenerative characteristics. Therefore it may be possible to beneficially affect excessive nerve activity by disrupting the conductive pathway of the nervous tissue. When disrupting nerve conductive pathways, it is particularly advantageous to avoid damage to neighboring nerves or organ tissue. The ability to direct and control energy dosage is well-suited to the treatment of nerve tissue. Whether in a heating or ablating energy dosage, the precise control of energy delivery as described and disclosed herein may be directed to the nerve tissue. Moreover, directed application of energy may suffice to target a nerve without the need to be in exact contact, as would be required when using a typical ablation probe. For example, eccentric heating may be applied at a temperature high enough to denature nerve tissue without causing ablation and without requiring the piercing of luminal tissue. However, it may also be desirable to configure the energy delivery surface of the present disclosure to pierce tissue and deliver ablating energy similar to an ablation probe with the exact energy dosage being controlled by a power control and generation apparatus.

In some embodiments, efficacy of the denervation treatment can be assessed by measurement before, during, and/or after the treatment to tailor one or more parameters of the treatment to the particular patient or to identify the need for additional treatments. For instance, a denervation system may include functionality for assessing whether a treatment has caused or is causing a reduction in neural activity in a target or proximate tissue, which may provide feedback for adjusting parameters of the treatment or indicate the necessity for additional treatments.

While many of the devices and methods described herein are discussed relative to renal nerve modulation, it is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, pain management, cardiac ablation, pulmonary vein isolation, tumor ablation, benign prostatic hyperplasia therapy, nerve excitation or blocking or ablation, modulation of muscle activity, hyperthermia or other warming of tissues, etc. The disclosed methods and apparatus can be applied to any relevant medical procedure, involving both human and non-human subjects. The term modulation refers to ablation and other techniques that may alter the function of affected nerves and other tissue.

FIG. 1 is a schematic view of an illustrative sympathetic nerve modulation system 10 in situ. System 10 may include a sympathetic nerve ablation device 12. Sympathetic nerve ablation device 12 may be used to ablate nerves (e.g., renal nerves) disposed adjacent to the kidney K (e.g., renal nerves disposed about a renal artery RA). In use, sympathetic nerve ablation device 12 may be advanced through a blood vessel such as the aorta A to a position within the renal artery RA. This may include advancing sympathetic nerve ablation device 12 through a guide sheath or catheter 14. System 10 may include one or more conductive element(s) 16 for providing power to the sympathetic nerve modulation device 12. A distal end of each of the conductive element(s) 16 may be attached to one or more electrodes (not shown) at a location at or near a distal end of the modulation device 12. A proximal end of conductive element(s) 16 may be connected to a control and power unit 18, which may supply the appropriate electrical energy to activate one or more energy delivery regions or electrodes disposed at or near a distal end of the modulation device 12. In addition, control and power unit 18 may also be utilized to supply/receive the appropriate electrical energy and/or signal to activate one or more sensors disposed at or near a distal end of the modulation device 12. When suitably activated, the energy delivery regions are capable of ablating tissue as described below and the sensors may be used to sense desired physical and/or biological parameters. In some instances, the energy delivery regions may include electrodes. The terms energy delivery region(s) and electrode(s) may be considered to be equivalent to elements capable of ablating adjacent tissue in the disclosure which follows. The disclosure of "adjacent tissue" is intended to cover any tissue located sufficiently proximate the electrode(s) for ablation, and the locations and distances involved are intended to vary depending on application and/or other factors. In some instances, return electrode patches 20 may be supplied on the legs or at another conventional location on the patient's body to complete the electrical circuit. Although, in some instances, return electrode patches 20 may not be necessary or supplied. In some embodiments, the modulation device 12 may include a proximal hub (not illustrated) which may include ports for a guidewire, an inflation fluid, etc.

The control and power unit 18 may include monitoring elements to monitor parameters such as power, voltage, pulse size, temperature, force, contact, pressure, impedance and/or shape and other suitable parameters, with sensors mounted along sympathetic nerve modulation device 12, as well as suitable controls for performing the desired procedure. In some embodiments, the power unit 18 may control a radiofrequency (RF) electrode. In some embodiments, the electrode may be configured to operate at a frequency of approximately 460 kHz. However, any desired frequency in the RF range may be used, for example, from 450-500 kHz. The electrode may be configured to operate at a suitable frequency and generate a suitable signal. It is further contemplated that other ablation devices may be used as desired, for example, but not limited to resistance heating, ultrasound, microwave, and laser devices and these devices may require that power be supplied by the power unit 18 in a different form.

Figure 2:
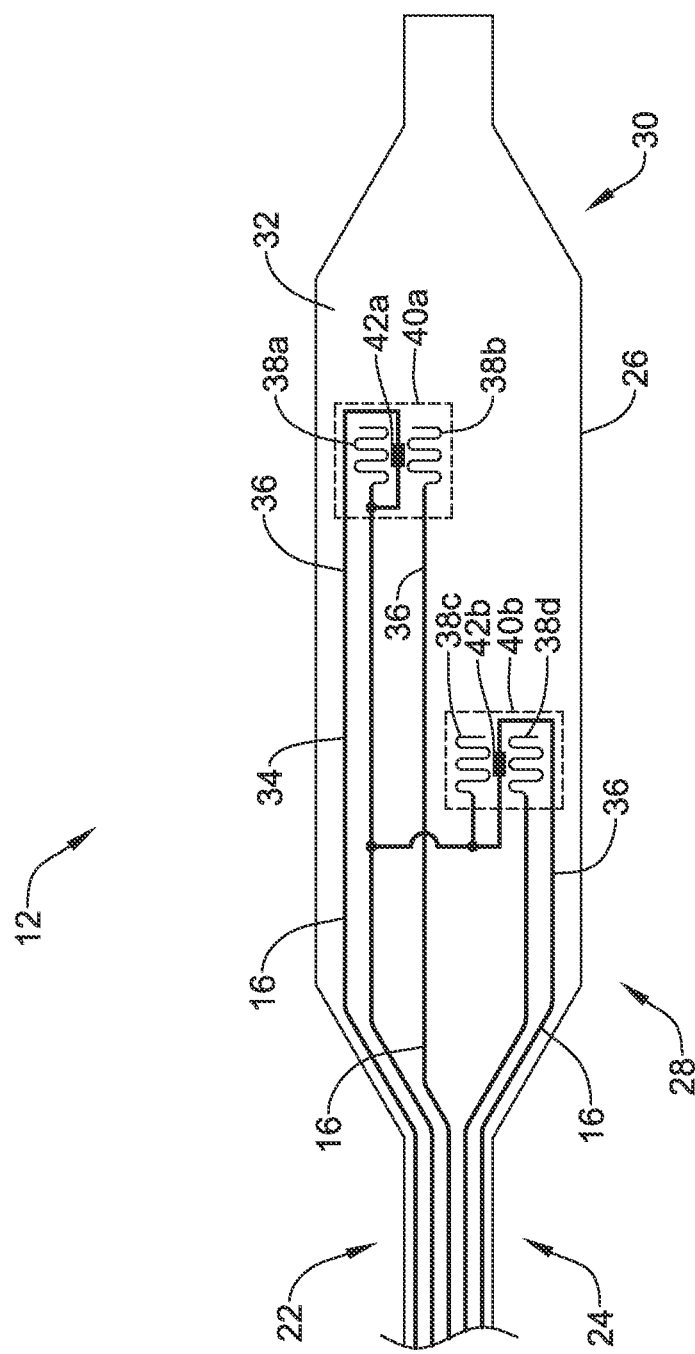
FIG. 2 is a side view of a distal portion of an illustrative medical device.

FIG. 2 illustrates a distal portion of a medical device such as sympathetic nerve modulation device 12 in accordance with one embodiment. Sympathetic nerve modulation device 12 may be configured to deliver ablation energy, for example, radiofrequency energy, to a target region such as renal nerves. The device 12 may include an elongate shaft 22, an expandable member 26, such as a balloon, coupled to a distal end region 24 of the elongate shaft 22, and one or more electrical conductors 16 disposed on an exterior surface of the balloon 26. In some embodiments, the device 12 may further include one or more temperature sensors such as, but not limited to thermistors 42a, 42b, (collectively 42), for monitoring the temperature adjacent to a treatment region. While not explicitly shown, in some instances, the temperature sensors may be thermocouples. In such an instance, the wiring of the device may be modified to accommodate the thermocouples. For example, the thermocouples may require independent or filtered, but not shared, ground paths.

The elongate shaft 22 may have a long, elongated, flexible tubular configuration that may be inserted into a patient's body for a medical diagnosis/treatment. The elongate shaft 22 may extend proximally from the distal end region 24 to a proximal end configured to remain outside of a patient's body. Although not shown, the proximal end of the elongate shaft 22 may include a hub attached thereto for connecting other treatment devices or providing a port for facilitating other treatments. It is contemplated that the stiffness of the elongate shaft 22 may be modified to form a modulation device 12 for use in various vessel diameters and various locations within the vascular tree.

The elongate shaft 22 may include one or more lumens extending therethrough. In some embodiments, the elongate shaft 22 may include one or more guidewire or auxiliary lumens. In some instances, the elongate shaft 22 may include a separate lumen(s) (not shown) for infusion of fluids, such as saline or dye for visualization or for other purposes such as the introduction of a medical device, and so forth. The fluid may facilitate cooling of the modulation device 12 during the ablation procedure, in addition to the cooling of a body lumen. Further, the lumens may be configured in any way known in the art. For example, the lumen(s) may extend along the entire length of the elongate shaft 22 such as in an over-the-wire catheter or may extend only along a distal portion of the elongate shaft 22 such as in a single operator exchange (SOE) catheter. These examples are not intended to be limiting, but rather examples of some possible configurations. While not explicitly shown, the modulation device 12 may further include temperature sensors/wire, an infusion lumen, an inflation lumen, radiopaque marker bands, fixed guidewire tip, a guidewire lumen, and/or other components to facilitate the use and advancement of the device 12 within the vasculature. In some embodiments, an inflation lumen can be connected to a system to circulate fluid through the balloon 26 or to a system that supplies new fluid and collects the evacuated fluid.

The proximal end of the elongate shaft 22 may be located adjacent to the power and control unit 18 although this is not required. In some embodiments, the elongate shaft 22 may define generally a circular cross-section; however, other cross-sectional shapes such as rectangular, semicircular, oval, irregular, cylindrical, or the like may also be contemplated. In some instances, the elongate shaft 22 may have a cross-sectional configuration adapted to be received in a desired vessel. In addition, a hub may be connected to the proximal end region of the elongated shaft 22 to facilitate connection to the inflation system for inflating/deflating the balloon 26, and/or to facilitate insertion of the guidewire or other medical device therein.

The balloon 26 may include a proximal end region 28, distal end region 30, an outer surface 32, and an interior volume (not explicitly shown) for receiving an inflation fluid. In some instances, the balloon 26 may be a relatively non-compliant polyethylene terephthalate (PET) balloon. This is just an example. In other instances, the balloon 26 may be formed from a compliant material, such as, but not limited to polyurethane. In some instances, a compliant balloon may have a lower profile than a non-compliant balloon. In some embodiments, the sympathetic nerve modulation device 12 may include an inner elongate shaft (not explicitly shown) extending coaxially within the elongate shaft 22. The distal end 30 of the balloon 26 may be attached to the inner shaft while the proximal end 28 may be attached to the elongate shaft 22, although this is not required. The inner shaft may define a guidewire lumen while an annular region between the elongate shaft 22 and the inner shaft may define an inflation lumen. However, other configurations are contemplated. The balloon 26 may be coupled to the device through laser spotting, mechanical thermal bonding, adhesive, other known techniques, or later developed techniques. In other embodiments, the balloon 26 may be formed a unitary structure with, fixedly secured to, or otherwise coupled to, the device 12.

The interior volume may define a space for entry of a fluid or air that inflates the balloon 26 during operation. The interior volume may be connected to an external fluid system or reservoir (although not shown) to deliver or inject the fluid through an inflation lumen in the elongate shaft 22 to the balloon 26. The external fluid system can be disposed at any location that enables or otherwise facilitates entry of the fluid such as at the proximal end of the elongate shaft 22. In some instances, the inflation fluid may inflate the balloon 26 radially and/or longitudinally. During use, the balloon 26 can be filled with the fluid such as saline to allow expansion of the balloon to the desired size. While saline is one example fluid, other appropriate fluids include, but are not limited to, hypertonic solutions, contrast solution and mixtures of saline or hypertonic saline solutions with contrast solutions may also be used. In some instances, the balloon expansion may be monitored indirectly by monitoring the volume of fluid introduced into the system or may be monitored through radiographic or other known, related art, or later developed techniques.

One or more conductive elements or electrical conductors 16, each having a proximal end region (not shown) and a distal end region 36, may extend from the proximal end region of the elongate shaft 22 to the balloon 26. The proximal end region of the electrical conductors 16 may be connected to the power and control element 18, which may supply the appropriate electrical energy to activate one or more energy delivery regions or electrodes disposed at or near a distal end of the sympathetic nerve modulation device 12. In some instances, the electrical conductors 16 may extend along the outer surface 32 of the balloon 26 as well as an outer surface of the elongate shaft 22, although this is not required. In some embodiments, the electrical conductors may be formed from an electrically conductive material, such as, but not limited to, copper, gold, silver, or copper clad, etc. These are just examples. In some instances, the electrical conductors 16 may be flexible, generally round, wires. However, this is not required. It is contemplated that the electrical conductors 16 may have any cross-sectional shape desired, such as, but not limited to, square, rectangular, oblong, polygonal, etc.

The electrical conductors 16 may be coated or otherwise covered with an insulator or insulating material 34. In some instances, the insulating material 34 may be a polymeric material, such as, but not limited to polyethylene terephthalate (PET), polyamides, polyesters, polyurethanes, fluoropolymers, or polyimides. These are just examples, other insulating materials, polymeric or otherwise, are also contemplated. It is contemplated that the electrical conductors 16 may be coupled to the elongate shaft 22 and/or balloon 26 using any known technique, such as, but not limited to thermal bonding, adhesive bonded, solvent bonding, or any other currently known, related art, and/or later developed techniques. It is contemplated that electrical conductors 16 and/or energy delivery regions 38 may be secured to the balloon 26 without the use of a polymeric foil backing. The absence of a polymeric backing may reduce the amount of force required to withdraw the balloon 26 into a retrieval sheath or guide sheath (not shown).

In some instances, a portion of the insulating material 34 may be removed to define one or more energy delivery regions 38a, 38b, 38c, 38d (collectively 38). The portions of the electrical conductors 16 forming the energy delivery regions 38 may be wound, coiled, or positioned in any manner desired such as, but not limited to, serpentine, spiral or the like. This may increase surface area of the energy delivery regions 38 for effective ablation. However, this is not required. It is contemplated that the energy delivery regions 38 may be straight regions of the electrical conductors 16.

In some embodiments, the electrical conductors 16 and the energy delivery regions 38 may be arranged to deliver energy in a bipolar mode, where energy is delivered between the energy delivery regions 38 which are placed closely together on the balloon 26 and no external ground pads are needed. For example, the energy delivery regions 38 may be arranged in a fashion to form a number of bipolar pairs. In the embodiment of FIG. 2, a first bipolar pair 40a and a second bipolar pair 40b (collectively 40) are shown. The first bipolar pair 40a may be formed by a first energy delivery region 38a and a second different energy delivery region 38b. The second bipolar pair 40b may be formed by a third energy delivery region 38c and a fourth energy delivery region 38d. A thermistor 42a, or other temperature sensing means, may be placed adjacent to the energy delivery regions 38a, 38b, and a thermistor 42b, or other temperature sensing means, may be placed adjacent to energy delivery regions 38c, 38d to monitor the temperature adjacent to the energy delivery regions 38. In some instances, the power and control unit 18 may control the delivery of energy based on the temperature adjacent to the treatment region.

In some instances, the energy delivery regions 38a, 38b, may be placed in close proximity to each other and may engage a tissue area. Energy delivery region 38a may act as the active energy delivery region and energy delivery regions 38b may act as the return path to complete the electrical circuit. Current may flow from the active energy delivery region 38a to the return energy delivery region 38b to deliver the RF energy to the target tissue area. In some instances, the reverse configuration may also be contemplated, where energy delivery region 38b may act as active energy delivery region and the energy delivery region 38a may act as return path to complete the electrical circuit. In a similar fashion, the second bipolar pair 40b may work to deliver RF energy to the target tissue. This bipolar approach allows precise and effective energy delivery, and provides treatment only where necessary. As will be discussed in more detail below, it is contemplated that the energy delivery regions 38 may be configured in a monopolar arrangement as well. In this instance, energy may travel between the energy delivery region 38 and a return (or ground) electrode 20 positioned on a patient's body.

Only two bipolar pairs 40a, 40b are shown in FIG. 2 for purposes of explanation. However, any suitable number of bipolar pairs 40 can be disposed on the balloon 26 for delivering the RF energy. For example, there can be one, two, three four, five, six, etc., bipolar pairs on the balloon 26. The energy delivery regions 38 and/or bipolar pairs 40 may be arranged about the circumference and/or length of the balloon 26 as desired. In some instances, the energy delivery regions 38 may be staggered along the length of the balloon 26. In other instances, the energy delivery regions 38 may be positioned at a similar position along the length of the balloon 26 and staggered about the circumference of the balloon 26. In some embodiments, the energy delivery regions 38 may be evenly positioned about the circumference of the balloon 26. In other embodiments, the energy delivery regions 38 may be asymmetrically positioned about the circumference of the balloon 26.

The number and configuration of electrical conductors 16 may depend on the number and configuration of the energy delivery regions 38, as well as the number of temperature sensors 42 provided and can vary accordingly. For example, the electrical conductors 16 may be positioned about the circumference of the balloon 26 so that the energy delivery regions 38 are located about the circumference of the inner surface of a vessel, such as the renal artery, when the balloon 26 is inflated. It can be appreciated that there are many variations in how the electrical conductors 16 can be arranged on the outer surface of the elongate shaft 22 and/or balloon 26.

During a modulation procedure, the nerve modulation device 12 may be advanced through the vasculature until the balloon 26 is positioned adjacent to a desired treatment region. The balloon 26 may then be inflated using an inflation fluid such that the outer surface 32 of the balloon 26 contacts the vessel wall or is in substantially close proximity to the vessel wall. When the balloon 26 is in an inflated state, the energy delivery regions 38 disposed on the balloon 26 may engage or be in close proximity to the vessel wall adjacent the target region. Electrical current may then be supplied to the energy delivery regions 38 through the electrical conductors 16 to deliver treatment energy to the target region. It should be understood that the control and power unit 18 may control the intensity of the electrical current and/or duration of the treatment to achieve the desired lesion size. For example, lesions may be formed in the range of from 1 millimeter (mm) to 6 mm by the active energy delivery regions 38. In some instances, the energy delivery regions 38 may be activated by supplying energy from control and power element 18 for a suitable length of time, such as less than 1 minute, 1 minute, 2 minutes, or more than 2 minutes. Once the procedure is finished at a particular location, the balloon 26 may be partially or entirely deflated and the elongate shaft 22 may be moved to a different location, such as a different longitudinal location with the same vessel or to a different vessel. The procedure may then be repeated as many times as necessary at the same location or at another location as desired to achieve the desired treatment.

Figure 3:
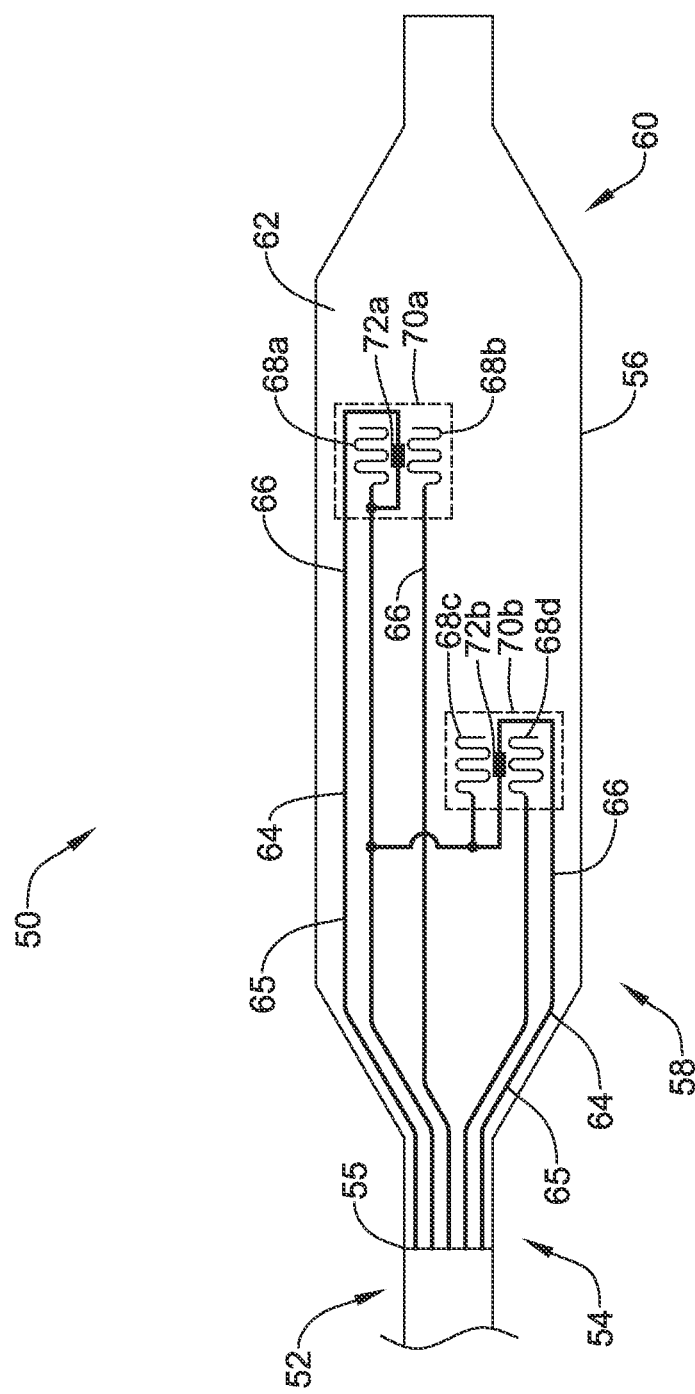
FIG. 3 is a side view of a distal portion of another illustrative medical device.

FIG. 3 illustrates a distal end portion of another nerve modulation device 50. Nerve modulation device 50 may be similar in form and function to nerve modulation device 12 described above. The device 50 may include an elongate shaft 52, a balloon 56 and one or more electrical conductors 64 disposed on an outer surface 62 of the balloon 56. In some embodiments, one or more temperature sensors such as thermistors 72a, 72b (collectively 72) may be disposed on an outer surface 62 of the balloon 56.

The elongate shaft 52 may extend proximally from the distal end region 54 to a proximal end configured to remain outside of a patient's body. The proximal end of the elongate shaft 52 may include a hub attached thereto for connecting other treatment devices or providing a port for facilitating other treatments. It is contemplated that the stiffness of the elongate shaft 52 may be modified to form a modulation device 50 for use in various vessel diameters and various locations within the vascular tree. The elongate shaft 52 may further include one or more lumens extending therethrough. For example, the elongate shaft 52 may include a guidewire lumen and/or one or more auxiliary lumens. The lumens may be configured in any way known in the art. While not explicitly shown, the modulation device 50 may further include temperature sensors/wire, an infusion lumen, radiopaque marker bands, fixed guidewire tip, a guidewire lumen, external sheath and/or other components to facilitate the use and advancement of the device 50 within the vasculature.

The balloon 56 may have a proximal end region 58, distal end region 60 and an interior volume (not explicitly shown) for receiving an inflation fluid. In some embodiments, the device 50 may include an inner elongate shaft (not shown). The distal end 60 of the balloon 56 may be attached to the inner shaft while the proximal end region 58 may be attached to the elongate shaft 52, although this is not required. The balloon 56 may be coupled to the device through laser spotting, mechanical thermal bonding, adhesive, other known techniques, or later developed techniques. In other embodiments, the balloon 56 may be formed a unitary structure with, fixedly secured to, or otherwise coupled to, the device 50. The inner shaft may define a guidewire lumen while the annular region between the elongate shaft 52 and the inner shaft may define an inflation lumen. The inflation lumen may define a space for entry of an inflation fluid that inflates the balloon 56 during operation. The inflation lumen may be connected to an external fluid system or reservoir (although not shown) to deliver or inject the fluid through the inflation lumen to the balloon 56. The external fluid system can be disposed at any location that enables or otherwise facilitates entry of the fluid such as at the proximal end of the elongate shaft 52. In some instances, the inflation fluid may inflate the balloon 56 radially and/or longitudinally.

One or more conductive elements or electrical conductors 64, each having a proximal end region (not shown) and a distal end region 66, may extend from the proximal end region of the elongate shaft 52 to the balloon 56. In some instances, the electrical conductors 64 may be positioned within the lumen of the elongate shaft 52, or the shaft wall, along at least a portion thereof. In some embodiments, at least a portion of the electrical conductors 64 may extend along the outer surface 62 of the balloon 56. It is contemplated that the electrical conductors 64 may extend within the lumen, or shaft wall, of the elongate shaft 52 and may exit the lumen at a joint 55 where the balloon 56 may be coupled to the elongate shaft 52. Other configurations are contemplated. For example, the electrical conductors 64 may transition from an interior position to an exterior position at any point along the length of the device 50 or may be disposed on the exterior of the device 50 along the entire length thereof.

The electrical conductors 64 may be coated or otherwise covered with an insulator or insulating material 65. In some instances, a portion of the insulating material 65 may be removed to define one or more energy delivery regions 68a, 68b, 68c, 68d (collectively 68). The portions of the electrical conductors 64 forming the energy delivery regions 68 may be wound, coiled, or positioned in any manner desired such as, but not limited to, serpentine, spiral or the like. This may increase surface area of the energy delivery regions 68 for effective ablation. However, this is not required. It is contemplated that the energy delivery regions 68 may be straight regions of the electrical conductors 64.

In some embodiments, the electrical conductors 64 and the energy delivery regions 68 may be arranged to deliver energy in a bipolar mode, where energy is delivered between the energy delivery regions 68 which are placed closely together on the balloon 56 and no external ground pads are needed. For example, the energy delivery regions 68 may be arranged in a fashion to form a number of bipolar pairs. In the embodiment of FIG. 3, a first bipolar pair 70a and a second bipolar pair 70b (collectively 70) are shown. The first bipolar pair 70a may be formed by a first energy delivery region 68a and a second different energy delivery region 68b. The second bipolar pair 70b may be formed by a third energy delivery region 68c and a fourth energy delivery region 68d. A thermistor 72a, or other temperature sensing means, may be placed adjacent to the energy delivery regions 68a, 68b, and a thermistor 72b, or other temperature sensing means, may be placed adjacent to energy delivery regions 68c, 68d to monitor the temperature adjacent to the energy delivery regions 68. In some instances, a power and control unit may control the delivery of energy based on the temperature adjacent to the treatment region. As will be discussed in more detail below, it is contemplated that the energy delivery regions 68 may be configured in a monopolar arrangement as well. In this instance, energy may travel between the energy delivery region 68 and a return (or ground) electrode positioned on a patient's body.

Only two bipolar pairs 70a, 70b are shown in FIG. 3 for purposes of explanation. However, any suitable number of bipolar pairs 70 can be disposed on the balloon 56 for delivering the RF energy. For example, there can be one, two, three four, five, six, etc., bipolar pairs on the balloon 56. The energy delivery regions 68 and/or bipolar pairs 70 may be arranged about the circumference and/or length of the balloon 56 as desired. In some instances, the energy delivery regions 68 may be staggered along the length of the balloon 56. In other instances, the energy delivery regions 68 may be positioned at a similar position along the length of the balloon 56 and staggered about the circumference of the balloon 56. In some embodiments, the energy delivery regions 68 may be evenly positioned about the circumference of the balloon 56. In other embodiments, the energy delivery regions 68 may be asymmetrically positioned about the circumference of the balloon 56.

The number and configuration of electrical conductors 64 may depend on the number and configuration of the energy delivery regions 68, as well as the number of temperature sensors 72 provided and can vary accordingly. For example, the electrical conductors 64 may be positioned about the circumference of the balloon 56 so that the energy delivery regions 68 are located about the circumference of the inner surface of a vessel, such as the renal artery, when the balloon 56 is inflated. It can be appreciated that there are many variations in how the electrical conductors 64 can be arranged on the outer surface of the elongate shaft 52 and/or balloon 56.

Figure 4:
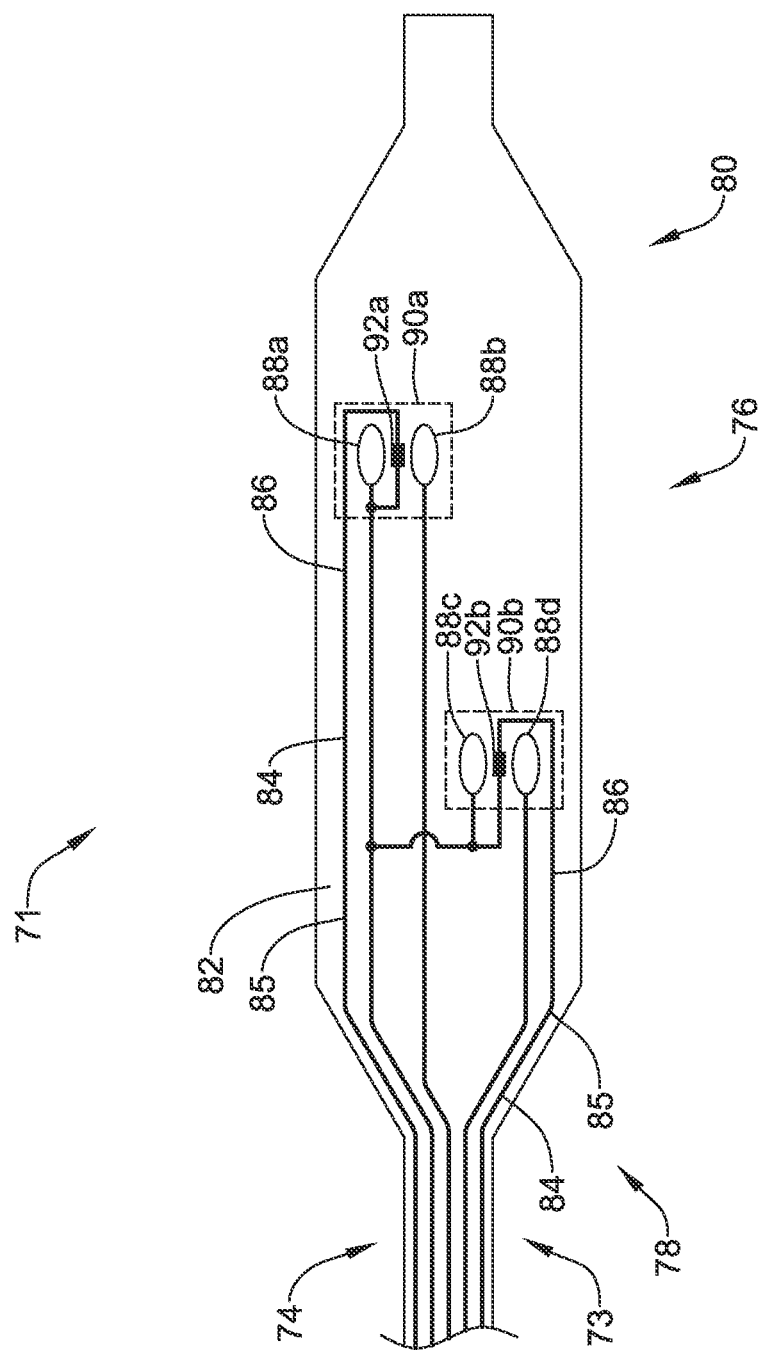
FIG. 4 is a side view of a distal portion of another illustrative medical device.

FIG. 4 illustrates a distal end portion of another nerve modulation device 71. Nerve modulation device 71 may be similar in form and function to nerve modulation devices 12, 50 described above. The device 71 may include an elongate shaft 73, a balloon 76 and one or more electrical conductors 84 disposed on an outer surface 82 of the balloon 76. In some embodiments, one or more temperature sensors such as thermistors 92a, 92b (collectively 92) may be disposed on an outer surface 82 of the balloon 76. While not explicitly shown, in some instances, the temperature sensors may be thermocouples. In such an instance, the wiring of the device may be modified to accommodate the thermocouples. For example, the thermocouples may require independent or filtered, but not shared, ground paths.

The elongate shaft 73 may extend proximally from the distal end region 74 to a proximal end configured to remain outside of a patient's body. The proximal end of the elongate shaft 73 may include a hub attached thereto for connecting other treatment devices or providing a port for facilitating other treatments. It is contemplated that the stiffness of the elongate shaft 73 may be modified to form a modulation device 71 for use in various vessel diameters and various locations within the vascular tree. The elongate shaft 73 may further include one or more lumens extending therethrough. For example, the elongate shaft 73 may include a guidewire lumen and/or one or more auxiliary lumens. The lumens may be configured in any way known in the art. While not explicitly shown, the modulation device 71 may further include temperature sensors/wire, an infusion lumen, radiopaque marker bands, fixed guidewire tip, a guidewire lumen, external sheath and/or other components to facilitate the use and advancement of the device 71 within the vasculature.

The balloon 76 may have a proximal end region 78, distal end region 80 and an interior volume (not explicitly shown) for receiving an inflation fluid. In some embodiments, the device 71 may include an inner elongate shaft (not shown). The distal end 80 of the balloon 76 may be attached to the inner shaft while the proximal end region 78 may be attached to the elongate shaft 73, although this is not required. The balloon 76 may be coupled to the device through laser spotting, mechanical thermal bonding, adhesive, other known techniques, or later developed techniques. In other embodiments, the balloon 76 may be formed a unitary structure with, fixedly secured to, or otherwise coupled to, the device 71. The inner shaft may define a guidewire lumen while the annular region between the elongate shaft 73 and the inner shaft may define an inflation lumen. The inflation lumen may define a space for entry of an inflation fluid that inflates the balloon 76 during operation. The inflation lumen may be connected to an external fluid system or reservoir (although not shown) to deliver or inject the fluid through the inflation lumen to the balloon 76. The external fluid system can be disposed at any location that enables or otherwise facilitates entry of the fluid such as at the proximal end of the elongate shaft 73. In some instances, the inflation fluid may inflate the balloon 76 radially and/or longitudinally.

One or more conductive elements or electrical conductors 84, each having a proximal end region (not shown) and a distal end region 86, may extend from the proximal end region of the elongate shaft 73 to the balloon 76. In some instances, the electrical conductors 84 may extend along the outer surface 82 of the balloon 86 as well as an outer surface of the elongate shaft 73, although this is not required. In other instances, the electrical conductors 84 may be positioned within the lumen of the elongate shaft 73, or the shaft wall, along at least a portion thereof. In some embodiments, at least a portion of the electrical conductors 84 may extend along the outer surface 82 of the balloon 76. Other configurations are contemplated. The electrical conductors 84 may be coated or otherwise covered with an insulator or insulating material 85.

In some embodiments, the distal end region 86 of some of the electrical conductors 84 may be connected to one or more electrodes 88a, 88b, 88c, 88d (collectively 88). The electrodes 88 may be discrete elements affixed to the outer surface 82 of the balloon 76 and connected to the electrical conductors 84. In some instances, the electrodes 88 may be soldered, welded, brazed, etc. to the electrical conductors. It is contemplated that the electrodes 88 may be formed of any material capable of delivering RF energy to the target tissue. While the electrodes 88 are illustrated as having a generally oval shape, it is contemplated that the electrodes 88 may take any shape desired, such as, but not limited to, square, round, rectangular, polygonal, etc.

In some embodiments, the electrical conductors 84 and the electrodes 88 may be arranged to deliver energy in a bipolar mode, where energy is delivered between the electrodes 88, which are placed closely together on the balloon 76, and no external ground pads are needed. For example, the electrodes 88 may be arranged in a fashion to form a number of bipolar pairs. In the embodiment of FIG. 4, a first bipolar pair 90a and a second bipolar pair 90b (collectively 90) are shown. The first bipolar pair 90a may be formed by a first electrode 88a and a second different electrode 88b. The second bipolar pair 90b may be formed by a third electrode 88c and a fourth electrode 88d. A thermistor 92a, or other temperature sensing means, may be placed adjacent to the electrodes 88a, 88b, and a thermistor 92b, or other temperature sensing means, may be placed adjacent to electrodes 88c, 88d to monitor the temperature adjacent to the electrodes 88. In some instances, a power and control unit may control the delivery of energy based on the temperature adjacent to the treatment region. As will be discussed in more detail below, it is contemplated that the electrodes 88 may be configured in a monopolar arrangement as well. In this instance, energy may travel between the electrode 88 and a return (or ground) electrode positioned on a patient's body.

Only two bipolar pairs 90*a*, 90*b* are shown in FIG. 4 for purposes of explanation. However, any suitable number of bipolar pairs 90 can be disposed on the balloon 76 for delivering the RF energy. For example, there can be one, two, three four, five, six, etc., bipolar pairs on the balloon 76. The electrodes 88 and/or bipolar pairs 90 may be arranged about the circumference and/or length of the balloon 76 as desired. In some instances, the electrodes 88 may be staggered along the length of the balloon 76. In other instances, the electrodes 88 may be positioned at a similar position along the length of the balloon 76 and staggered about the circumference of the balloon 76. In some embodiments, the electrodes 88 may be evenly positioned about the circumference of the balloon 76. In other embodiments, the electrodes 88 may be asymmetrically positioned about the circumference of the balloon 76.

The number and configuration of electrical conductors 84 may depend on the number and configuration of the electrodes 88, as well as the number of temperature sensors 92 provided and can vary accordingly. For example, the electrical conductors 84 may be positioned about the circumference of the balloon 76 so that the electrodes 88 are located about the circumference of the inner surface of a vessel, such as the renal artery, when the balloon 76 is inflated. It can be appreciated that there are many variations in how the electrical conductors 84 can be arranged on the outer surface of the elongate shaft 73 and/or balloon 76.

Figure 5:
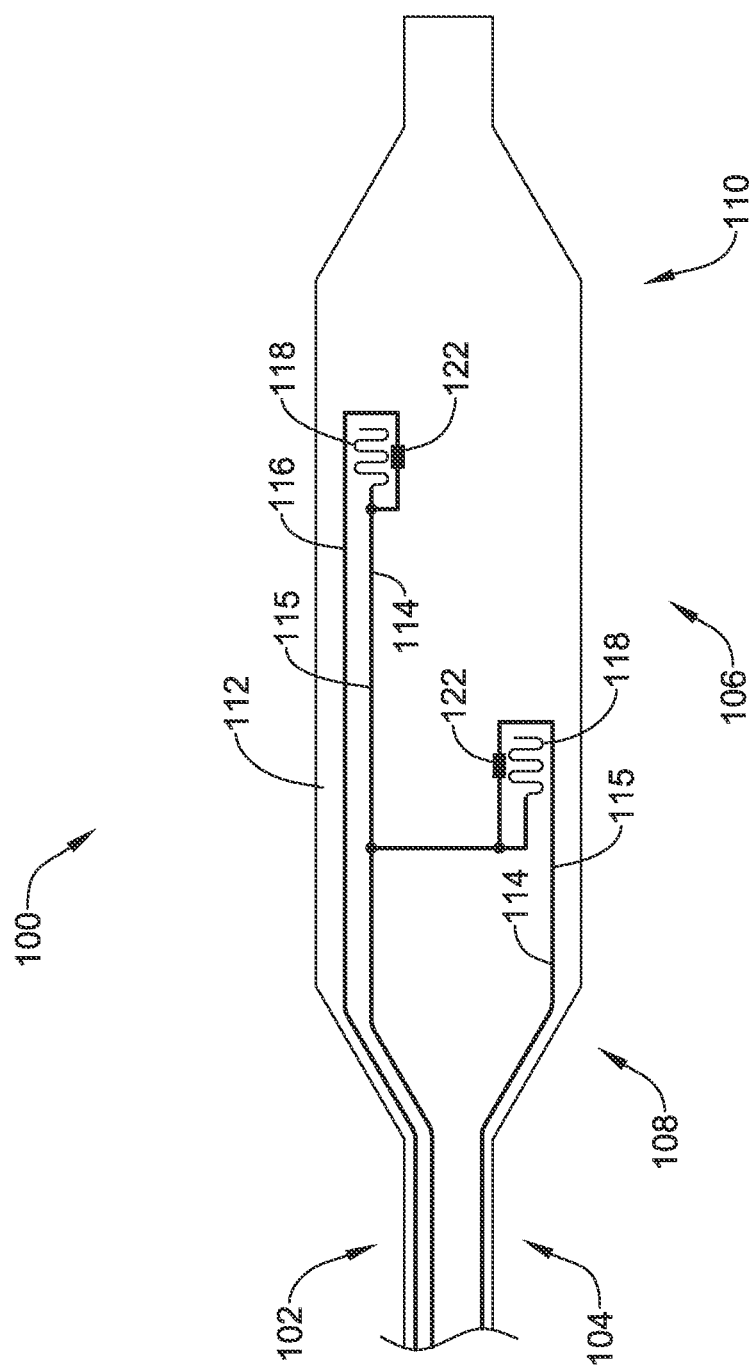
FIG. 5 is a side view of a distal portion of another illustrative medical device.

FIG. 5 illustrates a distal end portion of another nerve modulation device 100. Nerve modulation device 100 may be similar in form and function to nerve modulation devices 12, 50, 71 described above. The device 100 may include an elongate shaft 102, a balloon 106 and one or more electrical conductors 114 disposed on an outer surface 142 of the balloon 106. In some embodiments, one or more temperature sensors such as thermistors 122 may be disposed on an outer surface 112 of the balloon 106. While not explicitly shown, in some instances, the temperature sensors may be thermocouples. In such an instance, the wiring of the device may be modified to accommodate the thermocouples. For example, the thermocouples may require independent or filtered, but not shared, ground paths.

The elongate shaft 102 may extend proximally from the distal end region 104 to a proximal end configured to remain outside of a patient's body. The proximal end of the elongate shaft 102 may include a hub attached thereto for connecting other treatment devices or providing a port for facilitating other treatments. It is contemplated that the stiffness of the elongate shaft 102 may be modified to form a modulation device 100 for use in various vessel diameters and various locations within the vascular tree. The elongate shaft 102 may further include one or more lumens extending therethrough. For example, the elongate shaft 102 may include a guidewire lumen and/or one or more auxiliary lumens. The lumens may be configured in any way known in the art. While not explicitly shown, the modulation device 100 may further include temperature sensors/wire, an infusion lumen, radiopaque marker bands, fixed guidewire tip, a guidewire lumen, external sheath and/or other components to facilitate the use and advancement of the device 100 within the vasculature.

The balloon 106 may have a proximal end region 108, distal end region 110 and an interior volume (not explicitly shown) for receiving an inflation fluid. In some embodiments, the device 100 may include an inner elongate shaft (not shown). The distal end 110 of the balloon 106 may be attached to the inner shaft while the proximal end region 108 may be attached to the elongate shaft 102, although this is not required. The balloon 106 may be coupled to the device through laser spotting, mechanical thermal bonding, adhesive, other known techniques, or later developed techniques. In other embodiments, the balloon 106 may be formed a unitary structure with, fixedly secured to, or otherwise coupled to, the device 100. The inner shaft may define a guidewire lumen while the annular region between the elongate shaft 102 and the inner shaft may define an inflation lumen. The inflation lumen may define a space for entry of an inflation fluid that inflates the balloon 106 during operation. The inflation lumen may be connected to an external fluid system or reservoir (although not shown) to deliver or inject the fluid through the inflation lumen to the balloon 106. The external fluid system can be disposed at any location that enables or otherwise facilitates entry of the fluid such as at the proximal end of the elongate shaft 102. In some instances, the inflation fluid may inflate the balloon 106 radially and/or longitudinally.

One or more conductive elements or electrical conductors 114, each having a proximal end region (not shown) and a distal end region 116, may extend from the proximal end region of the elongate shaft 102 to the balloon 106. In some instances, the electrical conductors 114 may extend along the outer surface 112 of the balloon 86 as well as an outer surface of the elongate shaft 102, although this is not required. In other instances, the electrical conductors 114 may be positioned within the lumen of the elongate shaft 102, or the shaft wall, along at least a portion thereof. In some embodiments, at least a portion of the electrical conductors 114 may extend along the outer surface 112 of the balloon 106. Other configurations are contemplated.

The electrical conductors 114 may be coated or otherwise covered with an insulator or insulating material 115. In some instances, a portion of the insulating material 115 may be removed to define one or more energy delivery regions 118. The portions of the electrical conductors 114 forming the energy delivery portions 118 may be wound, coiled, or positioned in any manner desired such as, but not limited to, serpentine, spiral or the like. This may increase surface area of the energy delivery portions 118 for effective ablation. However, this is not required. It is contemplated that the energy delivery portions 118 may be straight regions of the electrical conductors 114. In some embodiments, the energy delivery portions 118 may be discrete electrodes affixed to the distal end region 116 of the electrical conductors 114.

In some embodiments, the electrical conductors 114 and the energy delivery regions 118 may be arranged to deliver energy in a monopolar mode, where energy is delivered between the energy delivery region 118 and an external ground pad, such as ground pad 20 shown in FIG. 1. A thermistor 122, or other temperatures sensing means, may be placed adjacent to the energy delivery regions 118 to monitor the temperature adjacent to the energy delivery regions 118. In some instances, a power and control unit may control the delivery of energy based on the temperature adjacent to the treatment region. It is contemplated that the energy delivery regions 118 may be configured in a bipolar arrangement as well. In this instance, energy may travel between adjacent energy delivery regions 118.

Only two energy delivery regions 118 are shown in FIG. 5 for purposes of explanation. However, any suitable number of energy delivery regions 118 can be disposed on the balloon 106 for delivering the RF energy. For example, there can be one, two, three four, five, six, etc., energy delivery regions 118 on the balloon 106. The energy delivery regions 118 may be arranged about the circumference and/or length of the balloon 106 as desired. In some instances, the energy delivery regions 118 may be staggered along the length of the balloon 106. In other instances, the energy delivery regions 118 may be positioned at a similar position along the length of the balloon 106 and staggered about the circumference of the balloon 106. In some embodiments, the energy delivery regions 118 may be evenly positioned about the circumference of the balloon 106. In other embodiments, the energy delivery regions 118 may be asymmetrically positioned about the circumference of the balloon 106.

The number and configuration of electrical conductors 114 may depend on the number and configuration of the energy delivery regions 118, as well as the number of temperature sensors 122 provided and can vary accordingly. For example, the electrical conductors 114 may be positioned about the circumference of the balloon 106 so that the energy delivery regions 118 are located about the circumference of the inner surface of a vessel, such as the renal artery, when the balloon 106 is inflated. It can be appreciated that there are many variations in how the electrical conductors 114 can be arranged on the outer surface of the elongate shaft 102 and/or balloon 106.

Figure 6:
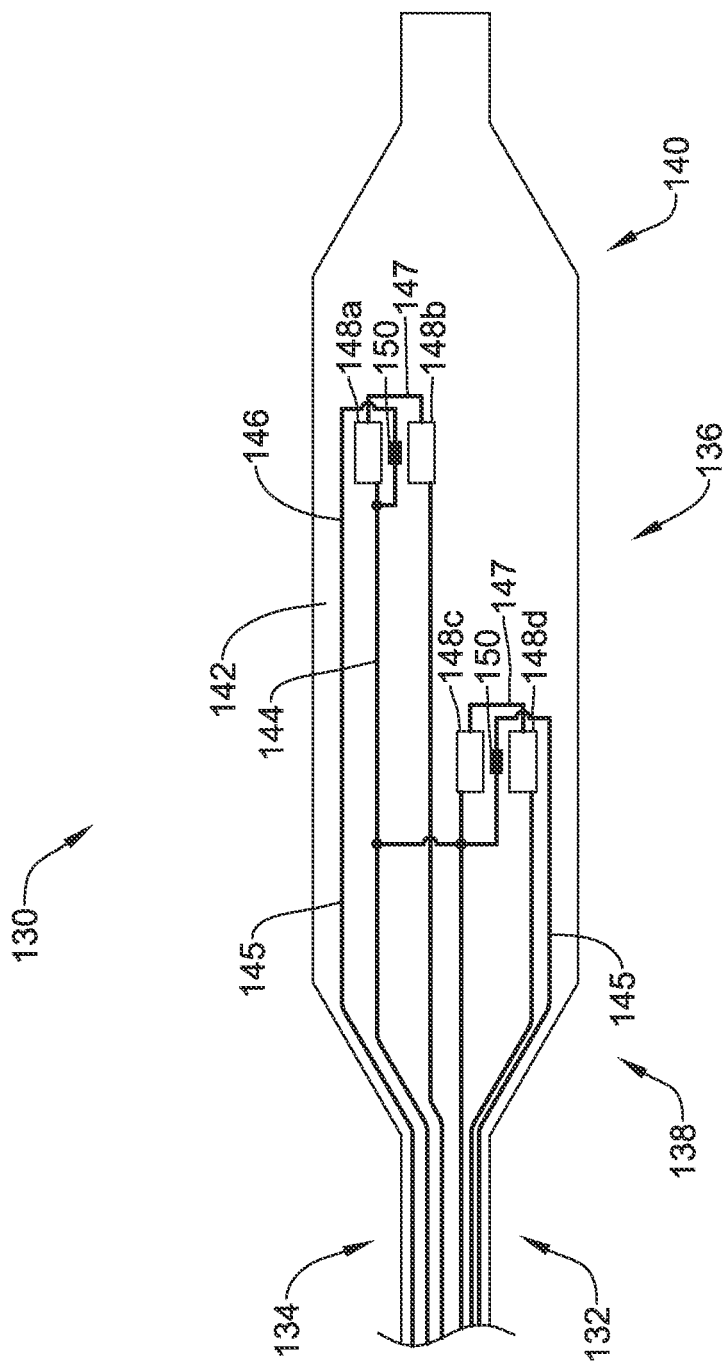
FIG. 6 is a side view of a distal portion of another illustrative medical device.

FIG. 6 illustrates a distal end portion of another nerve modulation device 130. Nerve modulation device 130 may be similar in form and function to nerve modulation devices 12, 50, 71, 100 described above. The device 130 may include an elongate shaft 132, a balloon 136 and one or more electrical conductors 144, 147 disposed on an outer surface 142 of the balloon 136. In some embodiments, one or more temperature sensors such as thermistors 150 may be disposed on an outer surface 142 of the balloon 136. While not explicitly shown, in some instances, the temperature sensors may be thermocouples. In such an instance, the wiring of the device may be modified to accommodate the thermocouples. For example, the thermocouples may require independent or filtered, but not shared, ground paths.

The elongate shaft 132 may extend proximally from the distal end region 134 to a proximal end configured to remain outside of a patient's body. The proximal end of the elongate shaft 132 may include a hub attached thereto for connecting other treatment devices or providing a port for facilitating other treatments. It is contemplated that the stiffness of the elongate shaft 132 may be modified to form a modulation device 130 for use in various vessel diameters and various locations within the vascular tree. The elongate shaft 132 may further include one or more lumens extending therethrough. For example, the elongate shaft 132 may include a guidewire lumen and/or one or more auxiliary lumens. The lumens may be configured in any way known in the art. While not explicitly shown, the modulation device 130 may further include temperature sensors/wire, an infusion lumen, radiopaque marker bands, fixed guidewire tip, a guidewire lumen, external sheath and/or other components to facilitate the use and advancement of the device 130 within the vasculature.

The balloon 136 may have a proximal end region 138, distal end region 140 and an interior volume (not explicitly shown) for receiving an inflation fluid. In some embodiments, the device 130 may include an inner elongate shaft (not shown). The distal end 140 of the balloon 136 may be attached to the inner shaft while the proximal end region 138 may be attached to the elongate shaft 132, although this is not required. The balloon 136 may be coupled to the device through laser spotting, mechanical thermal bonding, adhesive, other known techniques, or later developed techniques. In other embodiments, the balloon 136 may be formed a unitary structure with, fixedly secured to, or otherwise coupled to, the device 130. The inner shaft may define a guidewire lumen while the annular region between the elongate shaft 132 and the inner shaft may define an inflation lumen. The inflation lumen may define a space for entry of an inflation fluid that inflates the balloon 136 during operation. The inflation lumen may be connected to an external fluid system or reservoir (although not shown) to deliver or inject the fluid through the inflation lumen to the balloon 136. The external fluid system can be disposed at any location that enables or otherwise facilitates entry of the fluid such as at the proximal end of the elongate shaft 132. In some instances, the inflation fluid may inflate the balloon 136 radially and/or longitudinally.

One or more conductive elements or electrical conductors 144, each having a proximal end region (not shown) and a distal end region 146, may extend from the proximal end region of the elongate shaft 132 to the balloon 136. In some instances, the electrical conductors 144 may extend along the outer surface 142 of the balloon 136 as well as an outer surface of the elongate shaft 132, although this is not required. In other instances, the electrical conductors 144 may be positioned within the lumen of the elongate shaft 132, or the shaft wall, along at least a portion thereof. In some embodiments, at least a portion of the electrical conductors 144 may extend along the outer surface 142 of the balloon 136. Other configurations are contemplated. The electrical conductors 144 may be coated or otherwise covered with an insulator or insulating material 145.

In some embodiments, the distal end region 146 of some of the electrical conductors 114 may be connected to one or more micro-resistors 148a, 148b, 148c, 148d (collectively 148). A first electrical conductor 144 may be connected to a first micro-resistor 148a. The first micro-resistor 148a may be connected to a second micro-resistor 148b through a second electrical conductor 147. Electrical conductor 147 may be coated or otherwise covered with an insulator or insulating material. Electrical conductor 147 may connect a pair of micro-resistors 148a, 148b in series. Electrical current may be delivered to the first micro-resistor 148a through and returned to a power unit through the second micro-resistor 148b. As current travels through the micro-resistors 148a, 148b, the micro-resistors 148 may generate heat used to modulate the target tissue. In some instances, micro-resistors 148a, 148b may be configured as a single micro-resistor sized and shaped to extend around two or more sides of the temperature sensing element 150. Micro-resistors 148c, 148d may be configured in a similar manner to micro-resistors 148a, 148b.

While the micro-resistors 148 have been represented with a rectangular shape, it is contemplated that the micro-resistors 148 may take the size and shape of any known micro-resistor. It is further contemplated that micro-resistors 148 may take the form of other heating elements. A thermistor 150, or other temperatures sensing means, may be placed adjacent to the micro-resistors 148 to monitor the temperature adjacent to the micro-resistors 148. In some instances, a power and control unit may control the delivery of energy based on the temperature adjacent to the treatment region.

Only four micro-resistors 148 are shown in FIG. 6 for purposes of explanation. However, any suitable number of micro-resistors 148 can be disposed on the balloon 136 for delivering the modulation energy. For example, there can be one, two, three four, five, six, etc., micro-resistors 148 on the balloon 136. The micro-resistors 148 may be arranged about the circumference and/or length of the balloon 136 as desired. In some instances, the micro-resistors 148 may be staggered along the length of the balloon 136. In other instances, the micro-resistors 148 may be positioned at a similar position along the length of the balloon 136 and staggered about the circumference of the balloon 136. In some embodiments, the micro-resistors 148 may be evenly positioned about the circumference of the balloon 136. In other embodiments, the micro-resistors 148 may be asymmetrically positioned about the circumference of the balloon 136.

The number and configuration of electrical conductors 144, 147 may depend on the number and configuration of the micro-resistors 148, as well as the number of temperature sensors 150 provided and can vary accordingly. For example, the electrical conductors 144 may be positioned about the circumference of the balloon 136 so that the micro-resistors 148 are located about the circumference of the inner surface of a vessel, such as the renal artery, when the balloon 136 is inflated. It can be appreciated that there are many variations in how the electrical conductors 144 can be arranged on the outer surface of the elongate shaft 132 and/or balloon 136.

Figure 7:
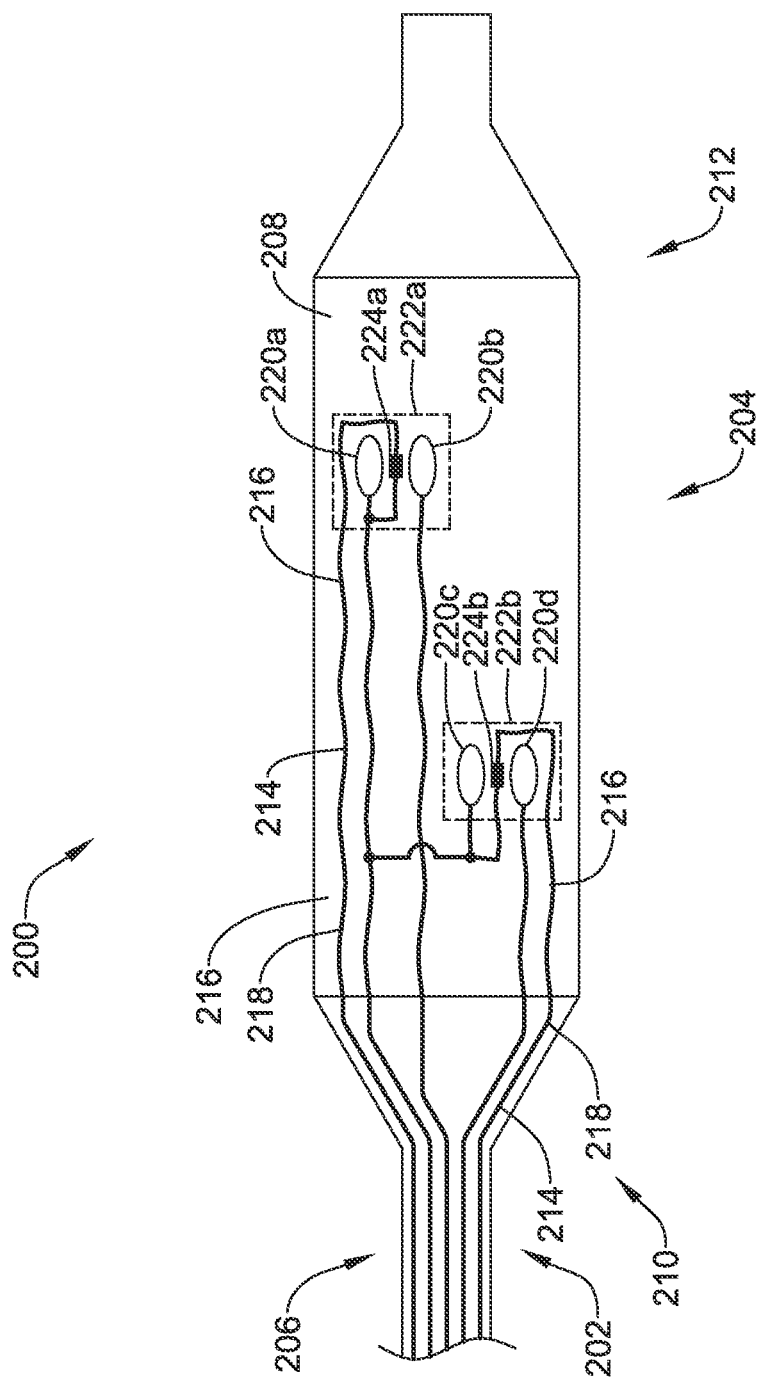
FIG. 7 is a side view of a distal portion of another illustrative medical device.

FIG. 7 illustrates a distal end portion of another nerve modulation device 200. Nerve modulation device 200 may be similar in form and function to nerve modulation devices 12, 50, 71, 100, 130, 200 described above. The device 200 may include an elongate shaft 202 and a balloon 204 adjacent to a distal end region 206 of the elongate shaft 202. A flexible substrate 208 may be disposed over the balloon 206. The elongate shaft 202 may extend proximally from the distal end region 206 to a proximal end configured to remain outside of a patient's body. The proximal end of the elongate shaft 202 may include a hub attached thereto for connecting other treatment devices or providing a port for facilitating other treatments. It is contemplated that the stiffness of the elongate shaft 202 may be modified to form a modulation device 200 for use in various vessel diameters and various locations within the vascular tree. The elongate shaft 202 may further include one or more lumens extending therethrough. For example, the elongate shaft 202 may include a guidewire lumen and/or one or more auxiliary lumens. The lumens may be configured in any way known in the art. While not explicitly shown, the modulation device 200 may further include temperature sensors/wire, an infusion lumen, radiopaque marker bands, fixed guidewire tip, a guidewire lumen, external sheath and/or other components to facilitate the use and advancement of the device 200 within the vasculature.

The balloon 204 may have a proximal end region 210, distal end region 212 and an interior volume (not explicitly shown) for receiving an inflation fluid. In some embodiments, the balloon 26 may be formed from a compliant material, such as, but not limited to polyurethane. In some instances, a compliant balloon may have a lower profile than a non-compliant balloon. In some embodiments, the device 200 may include an inner elongate shaft (not shown). The distal end 212 of the balloon 204 may be attached to the inner shaft while the proximal end region 210 may be attached to the elongate shaft 202, although this is not required. The balloon 204 may be coupled to the device through laser spotting, mechanical thermal bonding, adhesive, other known techniques, or later developed techniques. In other embodiments, the balloon 204 may be formed a unitary structure with, fixedly secured to, or otherwise coupled to, the device 200. The inner shaft may define a guidewire lumen while the annular region between the elongate shaft 202 and the inner shaft may define an inflation lumen. The inflation lumen may define a space for entry of an inflation fluid that inflates the balloon 204 during operation. The inflation lumen may be connected to an external fluid system or reservoir (although not shown) to deliver or inject the fluid through the inflation lumen to the balloon 204. The external fluid system can be disposed at any location that enables or otherwise facilitates entry of the fluid such as at the proximal end of the elongate shaft 202. In some instances, the inflation fluid may inflate the balloon 204 radially and/or longitudinally.

One or more conductive elements or electrical conductors 214, each having a proximal end region (not shown) and a distal end region 216, may extend from the proximal end region of the elongate shaft 202 to the balloon 204. In some instances, the electrical conductors 214 may bonded to a flexible substrate 208 which is attached to an outer surface of the balloon 204. The flexible substrate 208 may be formed from a compliant material, such as, but not limited to, polyurethane. In some instances, the flexible substrate 208 may be a tubular element which may be heat shrunk, expanded over the balloon, or otherwise attached to the balloon 204. It is contemplated that the electrical conductors 214 may be affixed to an outer diameter of a tubular flexible substrate, although this is not required. In other embodiments, the flexible substrate 208 may be a flat sheet which is wrapped around an outer surface 216 of the balloon 204 and bonded to itself and/or to the balloon 204. It is contemplated that the electrical conductors 214 may be affixed to an inner or outer surface of the flat sheet. The electrical conductors 214 may extend along the balloon 204 as well as an outer surface of the elongate shaft 202, although this is not required. In other instances, the electrical conductors 214 may be positioned within the lumen of the elongate shaft 202, or the shaft wall, along at least a portion thereof. In some embodiments, at least a portion of the electrical conductors 214 may extend along the outer surface 216 of the balloon 204. Other configurations are contemplated. The electrical conductors 214 may be coated or otherwise covered with an insulator or insulating material 218. In some instances, the electrical conductors 214 may be bonded to the flexible substrate 208 in a wound or serpentine fashion to allow the balloon 204 to expand or stretch without breaking the electrical conductors 214.

In some embodiments, the distal end region 216 of some of the electrical conductors 214 may be connected to one or more electrodes 220a, 220b, 220c, 220d (collectively 220). The electrodes 220 may be discrete elements affixed to the flexible substrate 208 and connected to the electrical conductors 214. In some instances, the electrodes 220 may be soldered, welded, brazed, etc. to the electrical conductors. It is contemplated that the electrodes 220 may be formed of any material capable of delivering RF energy to the target tissue. While the electrodes 220 are illustrated as having a generally oval shape, it is contemplated that the electrodes 220 may take any shape desired, such as, but not limited to, square, round, rectangular, polygonal, etc. It is contemplated that in some instances, the electrodes 220 may be formed from electrically conductive regions of the electrical conductors.

In some embodiments, the electrical conductors 214 and the electrodes 220 may be arranged to deliver energy in a bipolar mode, where energy is delivered between the electrodes 220, which are placed closely together, and no external ground pads are needed. For example, the electrodes 220 may be arranged in a fashion to form a number of bipolar pairs. In the embodiment of FIG. 7, a first bipolar pair 222a and a second bipolar pair 222b (collectively 222) are shown. The first bipolar pair 222a may be formed by a first electrode 220a and a second different electrode 220b. The second bipolar pair 222b may be formed by a third electrode 220c and a fourth electrode 220d. A thermistor 224a, or other temperature sensing means, may be placed adjacent to the electrodes 220a, 220b, and a thermistor 224b, or other temperature sensing means, may be placed adjacent to electrodes 220c, 220d to monitor the temperature adjacent to the electrodes 220. While not explicitly shown, in some instances, the temperature sensors may be thermocouples. In such an instance, the wiring of the device may be modified to accommodate the thermocouples. For example, the thermocouples may require independent or filtered, but not shared, ground paths. In some instances, a power and control unit may control the delivery of energy based on the temperature adjacent to the treatment region. As will be discussed in more detail below, it is contemplated that the electrodes 220 may be configured in a monopolar arrangement as well. In this instance, energy may travel between the electrode 220 and a return (or ground) electrode positioned on a patient's body.

Only two bipolar pairs 222a, 222b are shown in FIG. 7 for purposes of explanation. However, any suitable number of bipolar pairs 222 can be disposed on the balloon 204 for delivering the RF energy. For example, there can be one, two, three four, five, six, etc., bipolar pairs on the balloon 204. The electrodes 220 and/or bipolar pairs 222 may be arranged about the circumference and/or length of the balloon 204 as desired. In some instances, the electrodes 220 may be staggered along the length of the balloon 204. In other instances, the electrodes 220 may be positioned at a similar position along the length of the balloon 204 and staggered about the circumference of the balloon 204. In some embodiments, the electrodes 220 may be evenly positioned about the circumference of the balloon 204. In other embodiments, the electrodes 220 may be asymmetrically positioned about the circumference of the balloon 204.

The number and configuration of electrical conductors 214 may depend on the number and configuration of the electrodes 220, as well as the number of temperature sensors 224 provided and can vary accordingly. For example, the electrical conductors 214 may be positioned about the circumference of the balloon 204 so that the electrodes 220 are located about the circumference of the inner surface of a vessel, such as the renal artery, when the balloon 204 is inflated. It can be appreciated that there are many variations in how the electrical conductors 214 can be arranged on the outer surface of the elongate shaft 202 and/or balloon 204.

Portions of devices 12, 50, 71, 100, 130, 200 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel.

One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of devices 12, 50, 71, 100, 130, 200 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of device 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of devices 12, 50, 71, 100, 130, 200 to achieve the same result.

In some embodiments, a degree of Magnetic Resonance Imaging (MRI) compatibility is imparted into devices 12, 50, 71, 100, 130. For example, devices 12, 50, 71, 100, 130, 200 or portions thereof, may be made of a material that does not substantially distort the image and create substantial artifacts (i.e., gaps in the image). Certain ferromagnetic materials, for example, may not be suitable because they may create artifacts in an MRI image. Devices 12, 50, 71, 100, 130, 200 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for devices 12, 50, 71, 100, 130, 200 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosed subject matter may be manifested in a variety of forms other than the specific embodiments described and contemplated herein. Accordingly, departure in form and detail may be made without departing from the scope and spirit of the present disclosure as described in the appended.

What is claimed is:

1. A medical device, the medical device comprising:
    an elongate shaft having a proximal end region, a distal end region, and a lumen extending therebetween;
    an expandable member coupled to the distal end region of the elongate shaft, wherein the expandable member is an inflatable cylindrical balloon;
    one or more electrical conductors extending from the proximal end region to the expandable member, the one or more electrical conductors having a distal end region secured directly to an outer surface the expandable member; and
    one or more energy delivery regions positioned on the expandable member and coupled to the one or more electrical conductors;
    wherein the one or more energy delivery regions are formed from a distal portion of the one or more electrical conductors;
    wherein the one or more electrical conductors are each at least partially coated with an insulator;
    wherein the one or more energy delivery regions are defined by one or more regions of the one or more electrical conductors that are free of the insulator;
    wherein at least a portion of the one or more regions of the one or more electrical conductors that are free of the insulator is wound in a serpentine manner; and
    wherein the at least the portion of the one or more regions of the one or more electrical conductors that are free of the insulator is wound in the serpentine manner extending along a length of the inflatable cylindrical balloon.

2. The medical device of claim 1, wherein the one or more electrical conductors extend along an outer surface of the elongate shaft and an outer surface of the expandable member.

3. The medical device of claim 1, wherein the one or more electrical conductors extend within the lumen of the elongate shaft along at least a portion of a length of the elongate shaft and an outer surface of the expandable member.

4. The medical device of claim 1, wherein the one or more electrical conductors are adhesively secured to the expandable member.

5. The medical device of claim 1, wherein the one or more electrical conductors are thermally bonded to the expandable member.

6. The medical device of claim 1, wherein the one or more electrical conductors are solvent bonded to the expandable member.

7. The medical device of claim 1, wherein the insulator comprises a polyethylene terephthalate (PET), a polyamide, a polyester, a polyurethane, a fluoropolymer, or a polyimide.

8. The medical device of claim 1, wherein the one or more energy delivery regions comprise radiofrequency electrodes.

9. The medical device of claim 1, wherein the one or more energy delivery regions comprise at least two energy delivery regions and wherein the at least two energy delivery regions comprise a bipolar pair.

10. A medical device, the medical device comprising:
an elongate shaft having a proximal end region, a distal end region, and a lumen extending therebetween;
an inflatable cylindrical balloon coupled to the distal end region of the elongate shaft; and
one or more wire conductors having a proximal end and a distal end and covered with an insulating material, the one or more wire conductors extending from the proximal end region of the elongate shaft to an outer surface of the inflatable cylindrical balloon, wherein at least a portion of the one or more wire conductors is wound in a serpentine manner and is free from the insulating material defining one or more energy delivery regions adjacent the distal end of the one or more wire conductors and wherein the at least the portion of the one or more wire conductors is wound in the serpentine manner extending along a length of the inflatable cylindrical balloon.

11. The medical device of claim 10, wherein the insulating material comprises a polyethylene terephthalate (PET), a polyamide, a polyester, a polyurethane, a fluoropolymer, or a polyimide.

12. The medical device of claim 10, further comprising one or more temperature sensors.

13. The medical device of claim 12, wherein the one or more temperature sensors comprise thermistors.

14. The medical device of claim 10, wherein the one or more energy delivery regions comprise at least two energy delivery regions and wherein the at least two energy delivery regions comprise a bipolar pair.

15. A medical device, comprising:
an elongate shaft having a proximal end region, a distal end region, and a lumen extending therebetween;
an inflatable cylindrical balloon coupled to the distal end region of the elongate shaft;
one or more round wire conductors having a proximal end and a distal end and covered with an insulating material, the one or more round wire conductors extending from the proximal end region of the elongate shaft to the inflatable cylindrical balloon, wherein at least a portion of the one or more round wire conductors is wound in a serpentine manner and free from the insulating material defining one or more energy delivery regions adjacent the distal end of the one or more wire conductors; and
one or more temperature sensors positioned adjacent to at least one of the one or more energy delivery regions;
wherein the one or more energy delivery regions comprise at least two energy delivery regions and wherein the at least two energy delivery regions are arranged in bipolar pairs and wherein the at least the portion of the one or more round wire conductors is wound in the serpentine manner extending along a length of the inflatable cylindrical balloon.

16. The medical device of claim 15, wherein the one or more round wire conductors extend along an outer surface of the elongate shaft and an outer surface of the inflatable cylindrical balloon.

17. The medical device of claim 15 wherein the one or more round wire conductors extend within the lumen of the elongate shaft along at least a portion of a length of the elongate shaft and an outer surface of the inflatable cylindrical balloon.

* * * * *